US008071731B2

(12) United States Patent
Ellis et al.

(10) Patent No.: US 8,071,731 B2
(45) Date of Patent: *Dec. 6, 2011

(54) HUMANISED ANTI-MAG ANTIBODY OR FUNCTIONAL FRAGMENT THEREOF

(75) Inventors: Jonathan Henry Ellis, Stevenage (GB); Volker Germaschewski, Stevenage (GB)

(73) Assignee: Glaxo Group Limited (GB)

( * ) Notice: Subject to any disclaimer, the term of this patent is extended or adjusted under 35 U.S.C. 154(b) by 418 days.

This patent is subject to a terminal disclaimer.

(21) Appl. No.: 12/060,555

(22) Filed: Apr. 1, 2008

(65) Prior Publication Data

US 2009/0053214 A1    Feb. 26, 2009

Related U.S. Application Data

(62) Division of application No. 10/523,295, filed as application No. PCT/EP03/08749 on Aug. 5, 2003, now Pat. No. 7,612,183.

(30) Foreign Application Priority Data

| Aug. 6, 2002 | (GB) | .................................. 0218229.3 |
| Aug. 6, 2002 | (GB) | .................................. 0218230.1 |
| Aug. 6, 2002 | (GB) | .................................. 0218232.7 |
| Aug. 6, 2002 | (GB) | .................................. 0218234.3 |

(51) Int. Cl.
*C12P 21/08* (2006.01)
(52) U.S. Cl. ............. 530/387.3; 530/388.1; 530/388.15; 530/388.22
(58) Field of Classification Search .................... None
See application file for complete search history.

(56) References Cited

U.S. PATENT DOCUMENTS

| 4,873,316 | A | 10/1989 | Meade et al. |
| 5,154,924 | A | 10/1992 | Friden |
| 5,182,107 | A | 1/1993 | Friden |
| 5,250,414 | A | 10/1993 | Schwab et al. |
| 5,527,527 | A | 6/1996 | Friden |
| 5,792,743 | A | 8/1998 | Schachner |
| 5,833,988 | A | 11/1998 | Friden |
| 5,932,542 | A | 8/1999 | Filbin |
| 6,203,792 | B1 | 3/2001 | Filbin |
| 6,399,577 | B1 | 6/2002 | Filbin |
| 6,548,061 | B1 | 4/2003 | Steeves et al. |
| 6,576,607 | B1 | 6/2003 | Schachner |
| 7,612,183 | B2 | 11/2009 | Ellis et al. |
| 2004/0002790 | A1 | 1/2004 | Senn |
| 2004/0170627 | A1 | 9/2004 | Irving et al. |
| 2006/0165681 | A1 | 7/2006 | Ellis et al. |
| 2007/0269427 | A1 | 11/2007 | Irving et al. |
| 2008/0014195 | A1 | 1/2008 | Irving et al. |

FOREIGN PATENT DOCUMENTS

| EP | 308434 B | 9/1993 |
| WO | WO 00/63252 | 0/2000 |
| WO | WO 96/32959 | 0/1996 |
| WO | WO 95/22344 | 8/1995 |
| WO | WO 96/16990 | 6/1996 |
| WO | WO 97/01352 | 1/1997 |
| WO | WO 97/07810 | 3/1997 |
| WO | WO 95/12329 | 3/1998 |
| WO | WO 99/25378 | 5/1999 |
| WO | WO 99/53945 | 10/1999 |
| WO | WO 99/58679 | 11/1999 |
| WO | WO 00/31235 | 1/2000 |
| WO | WO 00/05364 | 2/2000 |
| WO | WO 00/43039 | 7/2000 |
| WO | WO 01/62907 | 8/2001 |
| WO | WO 02/062383 | 8/2002 |

OTHER PUBLICATIONS

Lamminmaki, et al., J. Biol. Chem., vol. 276(39) pp. 36687-36694 (2001).
DePascalis, et al., 2002;169:3076-3084.
Riechman et al; Reshaping human antibodies for therapy, Nature, vol. 332, Mar. 1988, pp. 323-327.
Angal, et al., Mol. Immunol, 1993, vol. 30, pp. 105-108.
Bard, et al., Nature Medicine, vol. 8, No. 8, pp. 916-919, Aug. 2000.
Bartsch, et al., Neuron, vol. 15 pp. 1375-1381 (1995).
Beattie, et al. neuron, 2002, vol. 36, pp. 375-386.
Belayev, et al., Brain Research, vol. 739 pp. 88-96 (1996).
Benincosa, et al., Journal of Pharmacology & Experimental Therapuetics, vol. 292, No. 2, pp. 810-816. (2000).
Bickel, et al. Proc Natl. Acad. Sci. USA, 1993, vol. 90, pp. 2618-2622.
Bickel, et al., Advanced Drug Delivery Reviews, vol. 46 pp. 247-274 (1996).
Birch and Lenox, Monoclonal Antibodies: Principles and Applications, John Wilet and Sons Inc. pp. 299-335 (1995).
Broadwell, et al. Exp. Neurol., 1996, vol. 142, pp. 47-65.
Chen, et al., Nature vol. 403 (6768) pp. 434-439 (2000).
Coloma, et al., Pharma Research, vol. 17(3) pp. 266-276 (2000).
Crowe, et al., Nature Medicine, 1997, vol. 3, pp. 73-76.
Debellard, et al., Molecular and Cellular Neuroscience, vol. 7, No. 7, pp. 89-101 (1996).
Dehouck, et al., J. Cell Biol., 1997, pp. 877-889.
Descamps, et al., Am. J. Physiol., 1996, vol. 270, H1149-H1158.
DeSouza, et al., Novel Therpeutic Modalities to Address Nondrugable Protein Interaction Target., Neuropsychopharmacology, 2009, 34, 142-158.
Duffy, et al. Brain Res., 1987, vol. 420, pp. 32-38. Friden, et al., J. Pharm. Exp. Ther., 1996, vol. 278, pp. 1491-1498.
Grandpre, et al., Nature, vol. 403(6768) pp. 439-444 (2000).
Green L.L. J Immunol Methods, Dec. 10, 1999, vol. 231, pp. 11-23.
Irving, et al., Acta Neuropathol (Berl), 2001, vol. 102, pp. 627-635.
Irving, et al., Journal of Cerebral Blood Flow and Metabolism, vol. 17, pp. 612-622 (1997).
Jakeman, et al., Exp. Neurol., vol. 154(1) pp. 170-184 (1998).
Kabat, et al., Sequences of Proteins of Immunological interest. U.S. Department of Health and Human Services, National Institutes of Health, 1987.
Kastrup, et al., Journal of the Neurological Sciences, vol. 166 pp. 91-99 (1999).

(Continued)

Primary Examiner — Gerald R Ewoldt
(74) Attorney, Agent, or Firm — Jason C. Fedon; William T. Han

(57) ABSTRACT

The present invention relates to altered antibodies to myelin associated glycoprotein (MAG), pharmaceutical formulations containing them and to the use of such antibodies in the treatment and/or prophylaxis of neurological diseases/disorders.

6 Claims, 7 Drawing Sheets

OTHER PUBLICATIONS

Kawamata, et al., Proc. Natl. Acad. Sci. USA, vol. 94(15) pp. 8179-8184.
Lassmann, et al., GLIA, vol. 19(2) pp. 104-110 (1997).
Li, et al., J. of Neurosci. Research, vol. 46(4) pp. 404-414 (1996).
Li, et al., J. of Neurosci. Research, vol. 51(2) pp. 210-217 (1998).
Li, et al., Nature, vol. 369(6483) pp. 747-750 (1994).
Lopate, et al., J. Neurol. Sci., vol. 188(1-2) pp. 67-72 (2001).
McKerracher, et al., Neuron, vol. 13 pp. 805-811 (1994).
Montag, et al, Neuron, vol. 13 pp. 229-246 (1994).
Moskowitz, et al., Brain Protection, Stroke, 2010; 41[suppl 1]:S85-S86.
Mukhopadhyay, et al., Neuron. vol. 13 pp. 757-767 (1994).
Niederost et al., J. of Neuroscience, vol. 22(23) pp. 10368-10376 (2002).
Pardridge, et al. Pharm. Res., 1995, vol. 12, pp. 807-816.
Poltorak, et al., J. of Cell Biology, vol. 105(4) pp. 1893-1899 (1987).
Prinjha, et al., Nature, vol. 403(6768) pp. 383-384 (2000).
Queen, et al., Proc. Natl. Acad. Sci. USA, 1989, vol. 86, pp. 10029-10032.
Ribotta, et al., J. Neurosci., vol. 20(13) pp. 5144-5152 (2000).
Roher, et al., Biochemistry, 2002, vol. 41, pp. 11080-11090.
Rouselle, et al., Journal of Pharmacology and Experimental Therapeutics, 2001, vol. 296, pp. 124-131.
Rouselle, et al., Mol. Pharm., 2000, vol. 57, pp. 679-686.
Saito, et al., Proc. Natl. Sci. USA, 1995, vol. 92, pp. 10227-10231.
Sambrook, et al., Molecular Cloning (A Laboratory Manual. Cold Spring Harbor Lab., 1989.
Sato, et al., Biochem. Biophys. Res. Comm., vol. 163(3) pp. 1473-1480 (1989).
Schafer, et al., Neuron, vol. 16(6) pp. 1107-1113 (1996).
Somogyvari-Vigh, et al., Regulatory Peptides, vol. 91 pp. 89-95 (2000).
Takle, et al., The identification of potent, selective and CNS penetraant furan-based inhibitors of—Raf kinase., 18 (2008) pp. 4373-4376.
Tang, et al., Mol. Cell. Neurosci., vol. 9(5-6) pp. 333-346 (1997).
Torigoe, et al., Exp. Neurology, vol. 150(2) pp. 254-262 (1997).
Umemori et al., Nature, vol. 367 pp. 572-576 (1994).
Valeriani et al., J. of Cerebral Blood Flow & Metabolism, vol. 20 pp. 765-771 (2000).
Vinson et al., Molecular and Cellular Neuroscience, vol. 22 pp. 344-352 (2003).
Wong et al., Nature Neuroscience, vol. 5(12) pp. 1302-1306 (2002).
Xu, et al., J. Biol. Chem.,1994, vol. 269, pp. 3469-3474.
Xu, et al., J. Neurosi., 2001, vol. 21, RC118.
Yin, et al., J. Neurosci., vol. 18(6) pp. 1953-1962 (1998).

Figure 1

MGWSCIILFLVATATGVHSEIQLVQSGPELKKPGETNKISCKASGYTFTNYGMNWVKQAPGKGLKW
MGWINTYTGEPTYADDFTGRFAFSLETSASTAYLQISNLKNEDTATYFCARNPINYYGINYEGYVM
DYWGQGTLVTVSSASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTHTCPPCPAPELAG
APSVFLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHEALHN
HYTQKSLSLSPGK  (SEQ ID No. 27)

Figure 2

MGWSCIILFLVATATGVHSNIMMTQSPSSLAVSAGEKVTMSCKSSHSVLYSSNQKNYLAWYQQKPG
QSPKLLIYWASTRESGVPDRFTGSGSGTDFTLTIINVHTEDLAVYYCHQYLSSLTFGTGTKLEIKR
TVAAPSVFIFPPSDEQLKSGTASVVCLLNNFYPREAKVQWKVDNALQSGNSQESVTEQDSKDSTYS
LSSTLTLSKADYEKHKVYACEVTHQGLSSPVTKSFNRGEC    (SEQ ID No. 28)

Figure 3

MGWSCIILFLVATATGVHSEIQLVQSGPELKKPGETNKISCKASGYTFTNYGMNWVKQAPGKGLKW
MGWINTYTGEPTYADDFTGRFAFSLETSASTAYLQISNLKNEDTATYFCARNPINYYGINYEGYVM
DYWGQGTLVTVSSASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTHTCPPCPAPELLG
GPSVFLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHEALHN
HYTQKSLSLSPGK  (SEQ ID No. 29)

Figure 5

Seq ID No: 30

MGWSCIILFLVATATGVHSQVQLVQSGSELKKPGASVKVSCKASGYTFTNYGM
NWVRQAPGQGLEWMGWINTYTGEPTYADDFTGRFVFSLDTSVSTAYLQISSL
KAEDTAVYYCARNPINYYGINYEGYVMDYWGQGTLVTVSSASTKGPSVFPLAP
SSKSTSGGTAALGCLVKDYFPEPVTVSWNSGALTSGVHTFPAVLQSSGLYSLSS
VVTVPSSSLGTQTYICNVNHKPSNTKVDKKVEPKSCDKTHTCPPCPAPELAGA
PSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQP
REPQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPGK

Seq ID No: 31

MGWSCIILFLVATATGVHSDIVMTQSPDSLAVSLGERATINCKSSHSVLYSSN
QKNYLAWYQQKPGQPPKLLIYWASTRESGVPDRFSGSGSGTDFTLTISSLQAE
DVAVYYCHQYLSSLTFGQGTKLEIKRTVAAPSVFIFPPSDEQLKSGTASVVCLL
NNFYPREAKVQWKVDNALQSGNSQESVTEQDSKDSTYSLSSTLTLSKADYEK
HKVYACEVTHQGLSSPVTKSFNRGEC

Seq ID No: 32

MGWSCIILFLVATATGVHSQVQLVQSGSELKKPGASVKVSCKASGYTFTNYGM
NWVRQAPGQGLEWMGWINTYTGEPTYADDFTGRFVFSLDTSVSTAYLQISSL
KAEDTAVYYCARNPINYYGINYEGYVMDYWGQGTLVTVSSASTKGPSVFPLAP
SSKSTSGGTAALGCLVKDYFPEPVTVSWNSGALTSGVHTFPAVLQSSGLYSLSS
VVTVPSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQP
REPQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPGK

Purified antibody material at concentrations determined by OD280

*Competition ELISA for binding to rat MAG-Fc fusion protein of two purified humanised antibodies and the non-humanised mouse monoclonal antibody*

HUMANISED ANTI-MAG ANTIBODY OR FUNCTIONAL FRAGMENT THEREOF

This application is a divisional of U.S. Ser. No. 10/523,295 filed on 3 Feb. 2005 now U.S. Pat. No. 7,612,183, which is a National Stage Application of PCT/EP03/08749 filed 5 Aug. 2003.

FIELD OF THE INVENTION

The present invention relates to altered antibodies that bind to myelin associated glycoprotein (MAG) and neutralise the function thereof, polynucleotides encoding such antibodies, pharmaceutical formulations containing said antibodies and to the use of such antibodies in the treatment and/or prophylaxis of neurological diseases. Other aspects, objects and advantages of the present invention will become apparent from the description below.

BACKGROUND OF THE INVENTION

Stroke is a major cause of death and disability in the Western World. There is no approved therapy for the treatment of stroke other than t-PA which has to be administered within 3 h of onset following a CT scan to exclude haemorrhage. To date most therapeutic agents directed towards the treatment of acute stroke (i.e. neuroprotection), have predominantly involved targeting glutamate receptors and their down stream signalling pathways known to be involved in acute cell death. However to date these strategies have proved unsuccessful in clinical trials and are often associated with dose-limiting side effects (Hill & Hachinski, *The Lancet,* 352: (suppl III) 10-14 (1998)). Therefore there is a need for novel approaches directed towards the amelioration of cell death following the cessation of blood flow.

Following the onset of stroke, some degree of spontaneous functional recovery is observed in many patients, suggesting that the brain has the (albeit limited) ability to repair and/or remodel following injury. Agents that have the potential to enhance this recovery may therefore allow intervention to be made much later (potentially days) following the onset of cerebral ischaemia. Agents which are able to offer both acute neuroprotection and enhance functional recovery may provide significant advantages over current potential neuroprotective strategies.

The mechanisms underlying functional recovery are currently unknown. The sprouting of injured or non-injured axons has been proposed as one possible mechanism. However, although in vivo studies have shown that treatment of spinal cord injury or stroke with neurotrophic factors results in enhanced functional recovery and a degree of axonal sprouting, these do not prove a direct link between the degree of axonal sprouting and extent of functional recovery (Jakeman, et al. 1998, *Exp. Neurol.* 154: 170-184, Kawamata et al. 1997, *Proc Natl Acad. Sci. USA.* 94:8179-8184, Ribotta, et al. 2000, *J Neurosci.* 20: 5144-5152). Furthermore, axonal sprouting requires a viable neuron. In diseases such as stroke which is associated with extensive cell death, enhancement of functional recovery offered by a given agent post stroke may therefore be through mechanisms other than axonal sprouting such as differentiation of endogenous stem cells, activation of redundant pathways, changes in receptor distribution or excitability of neurons or glia (Fawcett & Asher, 1999, *Brain Res. Bulletin,* 49: 377-391, Horner & Gage, 2000, *Nature* 407 963-970).

The limited ability of the central nervous system (CNS) to repair following injury is thought in part to be due to molecules within the CNS environment that have an inhibitory effect on axonal sprouting (neurite outgrowth). CNS myelin is thought to contain inhibitory molecules (Schwab M E and Caroni P (1988) *J. Neurosci.* 8, 2381-2193). Two myelin proteins, myelin-associated glycoprotein (MAG) and Nogo have been cloned and identified as putative inhibitors of neurite outgrowth (Sato S. et al (1989) *Biochem. Biophys. Res. Comm.* 163, 1473-1480; McKerracher L et al (1994) *Neuron* 13, 805-811; Mukhopadhyay G et al (1994) *Neuron* 13, 757-767; Torigoe K and Lundborg G (1997) *Exp. Neurology* 150, 254-262; Schafer et al (1996) *Neuron* 16, 1107-1113; WO9522344; WO9701352; Prinjha R et al (2000) *Nature* 403, 383-384; Chen M S et al (2000) *Nature* 403, 434-439; GrandPre T et al (2000) *Nature* 403, 439-444; US005250414A; WO200005364A1; WO0031235).

Myelin-associated glycoprotein is a cell surface transmembrane molecule expressed on the surface of myelin consisting of five extracellular immunoglobulin domains, a single transmembrane domain and an intracellular domain. MAG expression is restricted to myelinating glia in the CNS and peripheral nervous system (PNS). MAG is thought to interact with neuronal receptor(s) which mediate effects on the neuronal cytoskeleton including neurofilament phosphorylation and inhibition of neurite outgrowth in vitro. Although antagonists of MAG have been postulated as useful for the promotion of axonal sprouting following injury (WO9522344, WO9701352 and WO9707810), these claims are not supported by in vivo data. Furthermore, the role of MAG as an inhibitor of axonal sprouting from CNS neurons in vivo is not proven (Li C M et al (1994) *Nature* 369, 747-750; Montag, D et al (1994) *Neuron* 13, 229-246; Lassmann H et al (1997) *GLIA* 19, 104-110; Li C et al (1998)*J. Neuro. Res.* 51, 210-217; Yin X et al (1998) *J. Neurosci.* 18, 1953-1962; Bartsch U et al (1995) *Neuron* 15 1375-1381; Li M et al (1996) 46, 404-414).

Antibodies typically comprise two heavy chains linked together by disulphide bonds and two light chains. Each light chain is linked to a respective heavy chain by disulphide bonds. Each heavy chain has at one end a variable domain followed by a number of constant domains. Each light chain has a variable domain at one end and a constant domain at its other end. The light chain variable domain is aligned with the variable domain of the heavy chain. The light chain constant domain is aligned with the first constant domain of the heavy chain. The constant domains in the light and heavy chains are not involved directly in binding the antibody to antigen.

The variable domains of each pair of light and heavy chains form the antigen binding site. The variable domains on the light and heavy chains have the same general structure and each domain comprises a framework of four regions, whose sequences are relatively conserved, connected by three complementarity determining regions (CDRs) often referred to as hypervariable regions. The four framework regions largely adopt a beta-sheet conformation and the CDRs form loops connecting, and in some cases forming part of, the beta-sheet structure. The CDRs are held in close proximity by the framework regions and, with the CDRs from the other domain, contribute to the formation of the antigen binding site. CDRs and framework regions of antibodies may be determined by reference to Kabat et al ("Sequences of proteins of immunological interest" US Dept. of Health and Human Services, US Government Printing Office, 1987).

It has now been found that an anti-MAG monoclonal antibody, described (Poltorak et al (1987) *Journal of Cell Biology* 105, 1893-1899, DeBellard et al (1996) *Mol. Cell. Neurosci.* 7, 89-101; Tang et al (1997) *Mol. Cell. Neurosci.* 9, 333-346; Torigoe K and Lundborg G (1997) *Exp. Neurology* 150, 254-

262) and commercially available (MAB1567 (Chemicon)) when administered either directly into the brain or intravenously following focal cerebral ischaemia in the rat (a model of stroke), provides neuroprotection and enhances functional recovery. Therefore anti-MAG antibodies provide potential therapeutic agents for both acute neuroprotection as well as the promotion of functional recovery following stroke. This antibody is a murine antibody. Although murine antibodies are often used as diagnostic agents their utility as a therapeutic has been proven in only a few cases. Their limited application is in part due to the repeated administration of murine monoclonals to humans usually elicits human immune responses against these molecules. To overcome these intrinsic undesireable properties of murine monoclonals "altered" antibodies designed to incorporate regions of human antibodies have been developed and are well established in the art. For example, a humanised antibody contains complementarity determining regions ("CDR's") of non human origin and the majority of the rest of the structure is derived from a human antibody.

The process of neurodegeneration underlies many neurological diseases/disorders including acute diseases such as stroke, traumatic brain injury and spinal cord injury as well as chronic diseases including Alzheimer's disease, fronto-temporal dementias (tauopathies), peripheral neuropathy, Parkinson's disease, Huntington's disease and multiple sclerosis. Anti-MAG mabs therefore may be useful in the treatment of these diseases/disorders, by both ameliorating the cell death associated with these diseases/disorders and promoting functional recovery.

All publications, both journal and patent, disclosed in this present specification are expressly and entirely incorporated herein by reference.

BRIEF SUMMARY OF THE INVENTION

The invention provides an altered antibody or functional fragment thereof which binds to and neutralises MAG and comprises one or more of the following CDR's. The CDR's are identified as described by Kabat (Kabat et al. (1991) Sequences of proteins of immunological interest; Fifth Edition; US Department of Health and Human Services; NIH publication No 91-3242. CDRs preferably are as defined by Kabat but following the principles of protein structure and folding as defined by Chothia and Lesk, (Chothia et al., (1989) Conformations of immunoglobulin hypervariable regions; Nature 342, p 877-883) it will be appreciated that additional residues may also be considered to be part of the antigen binding region and are thus encompassed by the present invention.

Light Chain CDRs

| CDR | According to Kabat | |
|---|---|---|
| L1 | KSSHSVLYSSNQKNYLA | (SEQUENCE ID NO: 1) |
| L2 | WASTRES | (SEQUENCE ID NO: 2) |
| L3 | HQYLSSLT | (SEQUENCE ID NO: 3) |

Heavy Chain CDRs

| CDR | According to Kabat | |
|---|---|---|
| H1 | NYGMN | (SEQUENCE ID NO: 4) |
| H2 | WTNTYTGEPTYADDFTG | (SEQUENCE ID NO: 5) |
| H3 | NPINYYGINYEGYVMDY | (SEQUENCE ID NO: 6) |

The present invention also relates to an antibody which binds to the same epitope as an antibody having the CDRs described above. Competitive inhibition assays are used for mapping of the epitopes on an antigen. Thus there is also provided an anti-MAG antibody (altered or unaltered) which competitvely inhibits the binding of the altered antibody having the CDRs described supra to MAG, preferably human MAG.

In a further aspect, the present invention provides an altered antibody or functional fragment thereof which comprises a heavy chain variable domain which comprises one or more CDR's selected from CDRH1, CDRH2 and CDRH3 and/or a light chain variable domain which comprises one or more CDRs selected from CDRL1, CDRL2 and CDRL3.

The invention further provides an altered anti-MAG antibody or functional fragment thereof which comprises:
a) a heavy chain variable domain ($V_H$) which comprises in sequence CDRH1, CDRH2 and CDRH3,
and/or
b) a light chain variable domain ($V_L$) which comprises in sequence CDRL1, CDRL2 and CDRL3

A further aspect of the invention provides a pharmaceutical composition comprising an altered anti-MAG antibody of the present invention or functional fragment thereof together with a pharmaceutically acceptable diluent or carrier.

In a further aspect, the present invention provides a method of treatment or prophylaxis of stroke and other neurological diseases in a human which comprises administering to said human in need thereof an effective amount of an anti-MAG antibody of the invention or functional fragments thereof.

In another aspect, the invention provides the use of an anti-MAG antibody of the invention or a functional fragment thereof in the preparation of a medicament for treatment or prophylaxis of stroke and other neurological diseases.

In a further aspect, the present invention provides a method of inhibiting neurodegeneration and/or promoting functional recovery in a human patient afflicted with, or at risk of developing, a stroke or other neurological disease which comprises administering to said human in need thereof an effective amount of an anti-MAG antibody of the invention or a functional fragment thereof.

In a yet further aspect, the invention provides the use of an anti-MAG antibody of the invention or a functional fragment thereof in the preparation of a medicament for inhibiting neurodegeneration and/or promoting functional recovery in a human patient afflicted with, or at risk of developing, a stroke and other neurological disease.

Other aspects and advantages of the present invention are described further in the detailed description and the preferred embodiments thereof.

DESCRIPTION OF THE FIGURES

FIG. 1: Sequence of a mouse/human chimeric anti-MAG antibody heavy chain (SEQ ID No. 27).

FIG. 2: Sequence of a mouse/human chimeric anti-MAG antibody light chain (SEQ ID No. 28).

FIG. 3: Sequence of a mouse/human chimeric anti-MAG antibody heavy chain (SEQ q ID No. 29).

FIG. 5 Humanised anti-MAG antibody sequences

DETAILED DESCRIPTION OF THE INVENTION

Anti-MAG Antibody

Figure 4:
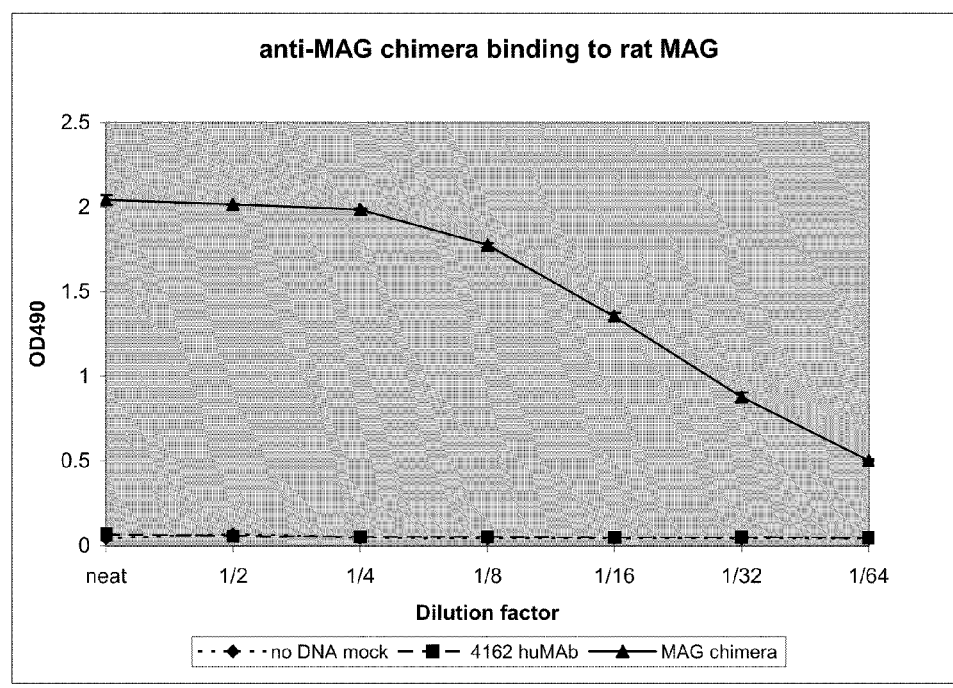
FIG. 4: Chimeric anti-MAG antibody binds to rat MAG

The altered antibody of the invention is preferably a monoclonal antibody (mAb) and is preferably chimeric, humanised or reshaped, of these humanised is particularly preferred.

The altered antibody preferably has the structure of a natural antibody or fragment thereof. The antibody may therefore comprise a complete antibody, a (Fab$^1$)$_2$ fragment, a Fab fragment, a light chain dimer or a heavy chain dimer. The antibody may be an IgG1, IgG2, IgG3, or IgG4; or IgM; IgA, IgE or IgD or a modified variant thereof. The constant domain of the antibody heavy chain may be selected accordingly. The light chain constant domain may be a kappa or lambda constant domain. Furthermore, the antibody may comprise modifications of all classes eg IgG dimers, Fc mutants that no longer bind Fc receptors or mediate Clq binding (blocking antibodies). The antibody may also be a chimeric antibody of the type described in WO86/01533 which comprises an antigen binding region and a non-immunoglobulin region. The antigen binding region is an antibody light chain variable domain or heavy chain variable domain. Typically the antigen binding region comprises both light and heavy chain variable domains. The non-immunoglobulin region is fused at its C terminus to the antigen binding region. The non-immunoglobulin region is typically a non-immunoglobullin protein and may be an enzyme, a toxin or protein having known binding specificity. The two regions of this type of chimeric antibody may be connected via a cleavable linker sequence. Immunoadhesins having the CDRS as hereinbefore described are also contemplated in the present invention.

The constant region is selected according to the functionality required. Normally an IgG1 will demonstrate lytic ability through binding to complement and/or will mediate ADCC (antibody dependent cell cytotoxicity). An IgG4 will be preferred if an non-cytototoxic blocking antibody is required. However, IgG4 antibodies can demonstrate instability in production and therefore is may be more preferable to modify the generally more stable IgG1. Suggested modifications are described in EPO307434 preferred modifications include at positions 235 and 237. The invention therefore provides a lytic or a non-lytic form of an antibody according to the invention In a preferred aspect the altered antibody is class IgG, more preferably IgG1.

In preferred forms therefore the antibody of the invention is a full length non-lytic IgG1 antibody having the CDRs described supra. In most preferred forms we provide a full length non-lytic IgG1 antibody having the CDRs of SEQ.I.D.NO: 13 and 16 and a full length non-lytic IgG1 antibody having the CDRs of SEQ.I.D.NO: 15 and 18.

In a further aspect, the invention provides polynucleotides encoding CDRH1, CDRH2, CDRH3, CDRL1, CDRL2 and CDRL3. Preferred polynucleotide sequences are Light chain CDRs

| CDR | |
|---|---|
| L1 | AAGAGCAGCCACAGCGTGCTGTACAGCAGCA ACCAGAAGAACTACCTGGCC (SEQUENCE ID NO: 7) |
| L2 | TGGGCCAGCACCCGCGAGAGC (SEQUENCE IDS NO: 8) |
| L3 | CACCAGTACCTGAGCAGCCTGACC (SEQUENCE ID NO: 9) |

Heavy chain CDRs

| CDR | |
|---|---|
| H1 | AACTACGGCATGAAC (SEQUENCE ID NO: 10) |
| H2 | TGGATCAACACCTACACCGGCGAGCCCACCT ACGCCGACGACTTCACCGGC (SEQUENCE ID NO: 11) |
| H3 | AACCCCATCAACTACTACGGCATCAACTACG AGGGCTACGTGATGGACTAC (SEQUENCE ID NO: 12) |

In a further aspect of the invention, there is provided a polynucleotide encoding a light chain variable region of an altered anti-MAG antibody including at least one CDR selected from CDRL1, CDRL2 and CDRL3, more preferably including all 3 CDRs in sequence.

In a further aspect of the invention, there is provided a polynucleotide encoding a heavy chain variable region of an altered anti-MAG antibody including at least one CDR selected from CDRH1, CDRH2 and CDRH3, more preferably including all 3 CDRs in sequence.

In a particularly preferred aspect, the anti-MAG antibody of the invention is a humanised antibody.

The invention therefore further provides a humanised antibody or functional fragment thereof that binds to and neutralises MAG which comprises a heavy chain variable region comprising one of the following amino acid sequences:

(SEQ ID No 13)
QVQLVQSGSELKKPGASVKVSCKASGYTFTNYGMNWVRQAPGQGLEWMGW

INTYTGEPTYADDFTGRFVFSLDTSVSTAYLQISSLKAEDTAVYYCARNP

INYYGINYEGYVMDYWGQGTLVTVSS.

(Sequence ID No 14)
QVQLVQSGSELKKPGASVKVSCKASGYTFTNYGMNWVRQAPGQGLEWMGW

INTYTGEPTYADDFTGRFVFSLDTSVSTAYLQISSLKAEDTAVYFCARNP

INYYGINYEGYVMDYWGQGTLVTVSS (sequence ID No 15)
QVQLVQSGSELKKPGASVKVSCKASGYTFTNYGMNWVRQAPGQGLEWMGW

INTYTGEPTYADDFTGRFVFSLDTSVSTAYLQISSLKAEDTATYFCARNP

INYYGINYEGYVMDYWGQGTLVTVSS

In a further aspect of the invention there is provided a humanised antibody or functional fragment thereof which binds to MAG which comprises the heavy chain variable region of Sequence ID No 13, 14 or 15 together with a light chain variable region comprising amino acid Sequences, Sequence ID No 16, 17, 18, or 19:

(SEQ ID No 16)
DIVMTQSPDSLAVSLGERATINCKSSHSVLYSSNQKNYLAWYQQKPGQPP

KLLIYWASTRESGVPDRFSGSGSGTDFTLTISSLQAEDVAVYYCHQYLSS

LTFGQGTKLEIKRTV (SEQ ID No 17)
DIVMTQSPDSLAVSLGERATINCKSSHSVLYSSNQKNYLAWYQQKPGQPP

KLLIYWASTRESGVPDRFSGSGSGTDFTLTIINLQAEDVAVYYCHQYLSS

LTFGQGTKLEIKRTV (SEQ ID No 18)
DIVMTQSPDSLAVSLGERATINCKSSHSVLYSSNQKNYLAWYQQKPGQPP

KLLIYWASTRESGVPDRFSGSGSGTDFTLTISSLHTEDVAVYYCHQYLSS

LTFGQGTKLEIKRTV (SEQ ID No 19)
DIVMTQSPDSLAVSLGERATINCKSSHSVLYSSNQKNYLAWYQQKPGQPP

KLLIYWASTRESGVPDRFSGSGSGTDFTLTIINLHTEDVAVYYCHQYLSS

LTFGQGTKLEIKRTV

In a further aspect of the present invention there is provided a humanised antibody comprising:
  a heavy chain variable fragment comprising SEQ ID No 13, 14 or 15
  and a constant part or fragment thereof of a human heavy chain and
  a light chain variable fragment comprising SEQ ID No 16, 17, 18 or 19 and a constant part or fragment thereof of a human light chain.

In a preferred aspect the humanised antibody is class IgG more preferably IgG1.

Preferred antibodies of the invention comprise:
  Heavy chain variable region comprising Seq ID No 13 and light chain variable region comprising Seq ID No 16;
  Heavy chain variable region comprising Seq ID No 13 and light chain variable region comprising Seq ID No 17;
  Heavy chain variable region comprising Seq ID No 13 and light chain variable region comprising Seq ID No 18;
  Heavy chain variable region comprising Seq ID No 13 and light chain variable region comprising Seq ID No 19.
  Heavy chain variable region Scomprising eq ID No 14 and light chain variable region comprising Seq ID No 16;
  Heavy chain variable region comprising Seq ID No 14 and light chain variable region comprising Seq ID No 17;
  Heavy chain variable region comprising Seq ID No 14 and light chain variable region comprising Seq ID No 18;
  Heavy chain variable region comprising Seq ID No 14 and light chain variable region comprising Seq ID No 19.
  Heavy chain variable region Scomprising eq ID No 15 and light chain variable region comprising Seq ID No 16;
  Heavy chain variable region comprising Seq ID No 15 and light chain variable region comprising Seq ID No 17;
  Heavy chain variable region comprising Seq ID No 15 and light chain variable region comprising Seq ID No 18;
  Heavy chain variable region comprising Seq ID No 15 and light chain variable region comprising Seq ID No 19.

In a further aspect, the invention provides polynucleotides encoding the heavy chain variable region comprising Sequence ID Nos 13, 14 and 15 and light chain variable regions comprising Sequence ID No 16, 17, 18 and 19.

Preferred polynucleotide Sequence encoding the amino acid Sequence SEQ ID NO 13 is (SEQ ID No 20)
CAGGTGCAGCTGGTGCAATCTGGGTCTGAGTTGAAGAAGCCTGGGGCCTC

AGTGAAGGTTTCCTGCAAGGCTTCTGGATACACCTTCACTAACTACGGCA

TGAACTGGGTGCGACAGGCCCCTGGACAAGGGCTTGAGTGGATGGGATGG

ATCAACACCTACACCGGCGAGCCCACCTACGCCGACGACTTCACCGGCCG

GTTTGTCTTCTCCTTGGACACCTCTGTCAGCACGGCATATCTGCAGATCA

GCAGCCTAAAGGCTGAGGACACTGCCGTGTATTACTGTGCGAGAAACCCC

ATCAACTACTACGGCATCAACTACGAGGGCTACGTGATGGACTACTGGGG

CCAGGGCACACTAGTCACAGTCTCCTCA

Preferred polynucleotide sequence encoding the amino acid Sequence ID No 14 is:

(SEQ ID No 21)
CAGGTGCAGCTGGTGCAATCTGGGTCTGAGTTGAAGAAGCCTGGGGCCTC

AGTGAAGGTTTCCTGCAAGGCTTCTGGATACACCTTCACTAACTACGGCA

TGAACTGGGTGCGACAGGCCCCTGGACAAGGGCTTGAGTGGATGGGATGG

ATCAACACCTACACCGGCGAGCCCACCTACGCCGACGACTTCACCGGCCG

GTTTGTCTTCTCCTTGGACACCTCTGTCAGCACGGCATATCTGCAGATCA

GCAGCCTAAAGGCTGAGGACACTGCCGTGTATTTCTGTGCGAGAAACCCC

ATCAACTACTACGGCATCAACTACGAGGGCTACGTGATGGACTACTGGGG

CCAGGGCACACTAGTCACAGTCTCCTCA

Preferred polynucleotide sequence encoding the amino acid Sequence ID No 15 is:

(SEQ ID No 22)
CAGGTGCAGCTGGTGCAATCTGGGTCTGAGTTGAAGAAGCCTGGGGCCTC

AGTGAAGGTTTCCTGCAAGGCTTCTGGATACACCTTCACTAACTACGGCA

TGAACTGGGTGCGACAGGCCCCTGGACAAGGGCTTGAGTGGATGGATCAA

CACCTACACCGGCGAGCCCACCTACGCCGACGACTTCACCGGCCGGTTTG

TCTTCTCCTTGGACACCTCTGTCAGCACGGCATATCTGCAGATCAGCAGC

CTAAAGGCTGAGGACACTGCCACCTATTTCTGTGCGAGAAACCCCATCAA

CTACTACGGCATCAACTACGAGGGCTACGTGATGGACTACTGGGGCCAGG

GCACACTAGTCACAGTCTCCTCA

Preferred polynucleotide sequence encoding the amino acid Sequence ID No 16 is:

(SEQ ID No 23)
GACATCGTGATGACCCAGTCTCCAGACTCCCTGGCTGTGTCTCTGGGCGA

GAGGGCCACCATCAACTGCAAGAGCAGCCACAGCGTGCTGTACAGCAGCA

ACCAGAAGAACTACCTGGCCTGGTACCAGCAGAAACCAGGACAGCCTCCT

AAGCTGCTCATTTACTGGGCATCTACCCGGGAATCCGGGGTCCCTGACCG

-continued
```
ATTCAGTGGCAGCGGGTCTGGGACAGATTTCACTCTCACCATCAGCAGCC

TGCAGGCTGAAGATGTGGCAGTTTATTACTGTCACCAGTACCTGAGCAGC

CTGACCTTTGGCCAGGGGACCAAGCTGGAGATCAAACGTACGGTG
```

Preferred polynucleotide sequence encoding SEQ ID No 17 is:

```
                                          (SEQ ID No 24)
GACATCGTGATGACCCAGTCTCCAGACTCCCTGGCTGTGTCTCTGGGCGA

GAGGGCCACCATCAACTGCAAGAGCAGCCACAGCGTGCTGTACAGCAGCA

ACCAGAAGAACTACCTGGCCTGGTACCAGCAGAAACCAGGACAGCCTCCT

AAGCTGCTCATTTACTGGGCATCTACCCGGGAATCCGGGGTCCCTGACCG

ATTCAGTGGCAGCGGGTCTGGGACAGATTTCACTCTCACCATCATCAACC

TGCAGGCTGAAGATGTGGCAGTTTATTACTGTCACCAGTACCTGAGCAGC

CTGACCTTTGGCCAGGGGACCAAGCTGGAGATCAAACGTACGGTG
```

Preferred polynucleotide encoding SEQ ID No 18 is:

```
                                          (SEQ ID No 25)
GACATCGTGATGACCCAGTCTCCAGACTCCCTGGCTGTGTCTCTGGGCGA

GAGGGCCACCATCAACTGCAAGAGCAGCCACAGCGTGCTGTACAGCAGCA

ACCAGAAGAACTACCTGGCCTGGTACCAGCAGAAACCAGGACAGCCTCCT

AAGCTGCTCATTTACTGGGCATCTACCCGGGAATCCGGGGTCCCTGACCG

ATTCAGTGGCAGCGGGTCTGGGACAGATTTCACTCTCACCATCAGCAGCC

TGCACACCGAAGATGTGGCAGTTTATTACTGTCACCAGTACCTGAGCAGC

CTGACCTTTGGCCAGGGGACCAAGCTGGAGATCAAACGTACGGTG
```

Preferred polynucleotide encoding SEQ ID No 19 is:

```
                                          (SEQ ID No 26)
GACATCGTGATGACCCAGTCTCCAGACTCCCTGGCTGTGTCTCTGGGCGA

GAGGGCCACCATCAACTGCAAGAGCAGCCACAGCGTGCTGTACAGCAGCA

ACCAGAAGAACTACCTGGCCTGGTACCAGCAGAAACCAGGACAGCCTCCT

AAGCTGCTCATTTACTGGGCATCTACCCGGGAATCCGGGGTCCCTGACCG

ATTCAGTGGCAGCGGGTCTGGGACAGATTTCACTCTCACCATCATCAACC

TGCACACCGAAGATGTGGCAGTTTATTACTGTCACCAGTACCTGAGCAGC

CTGACCTTTGGCCAGGGGACCAAGCTGGAGATCAAACGTACGGTG
```

"Neutralising" refers to inhibition, either total or partial, of MAG function including its binding to neurones and inhibition of neurite outgrowth.

"Altered antibody" refers to a protein encoded by an altered immunoglobulin coding region, which may be obtained by expression in a selected host cell. Such altered antibodies include engineered antibodies (e.g., chimeric, reshaped, humanized or vectored antibodies) or antibody fragments lacking all or part of an immunoglobulin constant region, e.g., Fv, Fab, or F(ab)$_2$ and the like.

"Altered immunoglobulin coding region" refers to a nucleic acid sequence encoding altered antibody. When the altered antibody is a CDR-grafted or humanized antibody, the sequences that encode the complementarity determining regions (CDRs) from a non-human immunoglobulin are inserted into a first immunoglobulin partner comprising human variable framework sequences. Optionally, the first immunoglobulin partner is operatively linked to a second immunoglobulin partner.

"First immunoglobulin partner" refers to a nucleic acid sequence encoding a human framework or human immunoglobulin variable region in which the native (or naturally-occurring) CDR-encoding regions are replaced by the CDR-encoding regions of a donor antibody. The human variable region can be an immunoglobulin heavy chain, a light chain (or both chains), an analog or functional fragments thereof. Such CDR regions, located within the variable region of antibodies (immunoglobulins) can be determined by known methods in the art. For example Kabat et al. (*Sequences of Proteins of Immunological Interest*, 4th Ed., U.S. Department of Health and Human Services, National Institutes of Health (1987)) disclose rules for locating CDRs. In addition, computer programs are known which are useful for identifying CDR regions/structures.

"Second immunoglobulin partner" refers to another nucleotide sequence encoding a protein or peptide to which the first immunoglobulin partner is fused in frame or by means of an optional conventional linker sequence (i.e., operatively linked). Preferably it is an immunoglobulin gene. The second immunoglobulin partner may include a nucleic acid sequence encoding the entire constant region for the same (i.e., homologous—the first and second altered antibodies are derived from the same source) or an additional (i.e., heterologous) antibody of interest. It may be an immunoglobulin heavy chain or light chain (or both chains as part of a single polypeptide). The second immunoglobulin partner is not limited to a particular immunoglobulin class or isotype. In addition, the second immunoglobulin partner may comprise part of an immunoglobulin constant region, such as found in a Fab, or F(ab)$_2$ (i.e., a discrete part of an appropriate human constant region or framework region). Such second immunoglobulin partner may also comprise a sequence encoding an integral membrane protein exposed on the outer surface of a host cell, e.g., as part of a phage display library, or a sequence encoding a protein for analytical or diagnostic detection, e.g., horseradish peroxidase, β-galactosidase, etc.

The terms Fv, Fc, Fd, Fab, or F(ab)$_2$ are used with their standard meanings (see, e.g., Harlow et al., *Antibodies A Laboratory Manual*, Cold Spring Harbor Laboratory, (1988)).

As used herein, an "engineered antibody" describes a type of altered antibody, i.e., a full-length synthetic antibody (e.g., a chimeric, reshaped or humanized antibody as opposed to an antibody fragment) in which a portion of the light and/or heavy chain variable domains of a selected acceptor antibody are replaced by analogous parts from one or more donor antibodies which have specificity for the selected epitope. For example, such molecules may include antibodies characterized by a humanized heavy chain associated with an unmodified light chain (or chimeric light chain), or vice versa. Engineered antibodies may also be characterized by alteration of the nucleic acid sequences encoding the acceptor antibody light and/or heavy variable domain framework regions in order to retain donor antibody binding specificity. These antibodies can comprise replacement of one or more CDRs (preferably all) from the acceptor antibody with CDRs from a donor antibody described herein.

A "chimeric antibody" refers to a type of engineered antibody which contains a naturally-occurring variable region (light chain and heavy chains) derived from a donor antibody in association with light and heavy chain constant regions derived from an acceptor antibody.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., Queen et al., *Proc. Natl Acad Sci USA,* 86: 10029-10032 (1989), Hodgson et al., *Bio/Technology,* 9:421 (1991)). A suitable human acceptor antibody may be one selected from a conventional database, e.g., the KABAT® database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanised antibodies—see for example EP-A-0239400 and EP-A-054951

"Reshaped human antibody" refers to an altered antibody in which minimally at least one CDR from a first human monoclonal donor antibody is substituted for a CDR in a second human acceptor antibody. Preferably all six CDRs are replaced. More preferably an entire antigen combining region (e.g., Fv, Fab or F(ab')$_2$) from a first human donor monoclonal antibody is substituted for the corresponding region in a second human acceptor monoclonal antibody. Most preferably the Fab region from a first human donor is operatively linked to the appropriate constant regions of a second human acceptor antibody to form a full length monoclonal antibody.

A "vectored antibody" refers to an antibody to which an agent has been attached to improve transport through the blood brain barrier (BBB). (Review see Pardridge; Advanced Drug Delivery Review 36, 299-321, 1999). The attachment may be chemical or alternatively the moeity can be engineered into the antibody. One example is to make a chimera with an antibody directed towards a brain capilliary endothelial cell receptor eg an anti-insulin receptor antibody or anti-transferrin receptor antibody (Saito et al (1995) *Proc. Natl. Acad. Sci. USA* 92 10227-31; Pardridge et al (1995) *Pharm. Res.* 12 807-816; Broadwell et al (1996) *Exp. Neurol.* 142 47-65; Bickel et al (1993) *Proc Natl. Acad. Sci. USA* 90, 2618-2622; Friden et al (1996) *J. Pharm. Exp. Ther.* 278 1491-1498, U.S. Pat. Nos. 5,182,107, 5,154,924, 5,833,988, 5,527,527). Once bound to the receptor, both components of the bispecific antibody pass across the BBB by the process of transcytosis. Alternatively the agent may be a ligand which binds such cell surface receptors eg insulin, transferrin or low density lipoprotein (Descamps et al (1996) *Am. J. Physiol.* 270 H1149-H1158; Duffy et al (1987) *Brain Res.* 420 32-38; Dehouck et al (1997) *J. Cell Biol.* 1997 877-889). Naturally occuring peptides such as penetratin and SynB1 and Syn B3 which are known to improve transport across the BBB can also be used (Rouselle et al (2000) *Mol. Pharm.* 57, 679-686 and Rouselle et al (2001) *Journal of Pharmacology and Experimental Therapeutics* 296, 124-131).

The term "donor antibody" refers to an antibody (monoclonal, or recombinant) which contributes the amino acid sequences of its variable regions, CDRs, or other functional fragments or analogs thereof to a first immunoglobulin partner, so as to provide the altered immunoglobulin coding region and resulting expressed altered antibody with the antigenic specificity and neutralizing activity characteristic of the donor antibody.

The term "acceptor antibody" refers to an antibody (monoclonal, or recombinant) heterologous to the donor antibody, which contributes all (or any portion, but preferably all) of the amino acid sequences encoding its heavy and/or light chain framework regions and/or its heavy and/or light chain constant regions to the first immunoglobulin partner. Preferably a human antibody is the acceptor antibody.

"CDRs" are defined as the complementarity determining region amino acid sequences of an antibody which are the hypervariable regions of immunoglobulin heavy and light chains. See, e.g., Kabat et al., *Sequences of Proteins of Immunological Interest,* 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate). The structure and protein folding of the antibody may mean that other residues are considered part of the antigen binding region and would be understood to be so by a skilled person. See for example Chothia et al., (1989) Conformations of immunoglobulin hypervariable regions; Nature 342, p 877-883. For convenience the CDR's as defined by Kabat in SEQ ID Nos 13-26 are underlined.

CDRs provide the majority of contact residues for the binding of the antibody to the antigen or epitope. CDRs of interest in this invention are derived from donor antibody variable heavy and light chain sequences, and include analogs of the naturally occurring CDRs, which analogs also share or retain the same antigen binding specificity and/or neutralizing ability as the donor antibody from which they were derived.

A "functional fragment" is a partial heavy or light chain variable sequence (e.g., minor deletions at the amino or carboxy terminus of the immunoglobulin variable region) which retains the same antigen binding specificity and/or neutralizing ability as the antibody from which the fragment was derived.

An "analog" is an amino acid sequence modified by at least one amino acid, wherein said modification can be chemical or a substitution or a rearrangement of a few amino acids (i.e., no more than 10), which modification permits the amino acid sequence to retain the biological characteristics, e.g., antigen specificity and high affinity, of the unmodified sequence. For example, (silent) mutations can be constructed, via substitutions, when certain endonuclease restriction sites are created within or surrounding CDR-encoding regions. The present invention contemplates the use of analogs of the antibody of the invention. It is well known that minor changes in amino acid or nucleic acid sequences may lead eg to an allelic form of the original protein which retains substantially similar properties. Thus analogs of the antibody of the invention includes those in which the CDRs in the hypervariable region of the heavy and light chains are at least 80% homologous, preferably at least 90% homologous and more preferably at least 95% homologous to the CDRs as defined above as CDRH1, CDRH2, CDRH3, CDRL1, CDRL2 and CDRL3 and retain MAG neutralising activity. Amino acid sequences are are at least 80% homologous if they have 80% identical amino acid residues in a like position when the sequences are aligned optimally, gaps or insertions being counted as non-identical residues. The invention also contemplates analogs of the antibodies of the invention wherein the framework regions are at least 80%, preferably at least 90% and more preferably at least 95% homologous to the framework regions set forth in Seq ID 1-5. Amino acid sequences are at least 80% homologous if they have 80% identical amino acid residues in a like position when the sequences are aligned optimally, gaps or insertions being counted as non-identical residues.

Analogs may also arise as allelic variations. An "allelic variation or modification" is an alteration in the nucleic acid sequence. Such variations or modifications may be due to degeneracy in the genetic code or may be deliberately engineered to provide desired characteristics. These variations or modifications may or may not result in alterations in any encoded amino acid sequence.

The term "effector agents" refers to non-protein carrier molecules to which the altered antibodies, and/or natural or synthetic light or heavy chains of the donor antibody or other fragments of the donor antibody may be associated by conventional means. Such non-protein carriers can include conventional carriers used in the diagnostic field, e.g., polystyrene or other plastic beads, polysaccharides, e.g., as used in the BIAcore [Pharmacia] system, or other non-protein substances useful in the medical field and safe for administration to humans and animals. Other effector agents may include a macrocycle, for chelating a heavy metal atom, or radioisotopes. Such effector agents may also be useful to increase the half-life of the altered antibodies, e.g., polyethylene glycol.

A neutralising antibody specific for MAG has been described (Poltorak et al (1987) *Journal of Cell Biology* 105, 1893-1899, DeBellard et al (1996) *Mol. Cell. Neurosci.* 7, 89-101; Tang et al (1997) *Mol. Cell. Neurosci.* 9, 333-346; Torigoe K and Lundborg G (1997) *Exp. Neurology* 150, 254-262) and is commercially available (MAB1567 (Chemicon)).

Alternatively, one can construct antibodies, altered antibodies and fragments, by immunizing a non-human species (for example, bovine, ovine, monkey, chicken, rodent (e.g., murine and rat), etc.) to generate a desirable immunoglobulin upon presentation with native MAG from any species against which antibodies cross reactive with human MAG can be generated, eg human or chicken. Conventional hybridoma techniques are employed to provide a hybridoma cell line secreting a non-human mAb to MAG. Such hybridomas are then screened for binding using MAG coated to 384- or 96-well plates, with biotinylated MAG bound to a streptavidin coated plate. or in a homogenous europium-APC linked immunoassay using biotinylated MAG.

A native human antibody can be produced in a human antibody mouse such as the "Xenomouse" (Abgenix) where the mouse immunoglobulin genes have been removed and genes encoding the human immunoglobulins have been inserted into the mouse chromosome. The mice are immunised as normal and develop an antibody reponse that is derived from the human genes. Thus the mouse produces human antibodies obviating the need to humanize the after selection of positive hybridomas. (See Green L. L., *J Immunol Methods* 1999 Dec. 10; 231(1-2):11-23)

The present invention also includes the use of Fab fragments or $F(ab')_2$ fragments derived from mAbs directed against MAG. These fragments are useful as agents protective in vivo. A Fab fragment contains the entire light chain and amino terminal portion of the heavy chain; and an $F(ab')_2$ fragment is the fragment formed by two Fab fragments bound by disulfide bonds. Fab fragments and $F(ab')_2$ fragments can be obtained by conventional means, e.g., cleavage of mAb with the appropriate proteolytic enzymes, papain and/or pepsin, or by recombinant methods. The Fab and $F(ab')_2$ fragments are useful themselves as therapeutic or prophylactic, and as donors of sequences including the variable regions and CDR sequences useful in the formation of recombinant or humanized antibodies as described herein.

The Fab and $F(ab')_2$ fragments can also be constructed via a combinatorial phage library (see, e.g., Winter et al., *Ann. Rev. Immunol.,* 12:433-455 (1994)) or via immunoglobulin chain shuffling (see, e.g., Marks et al., *Bio/Technology,* 10:779-783 (1992), which are both hereby incorporated by reference in their entirety.

Thus human antibody fragments (Fv, scFv, Fab) specific for MAG can be isolated using human antibody fragment phage display libraries. A library of bacteriophage particles, which display the human antibody fragment proteins, are panned against the MAG protein. Those phage displaying antibody fragments that bind the MAG are retained from the library and clonally amplified. The human antibody genes are then exicised from the specific bacteriophage and inserted into human IgG expression constructs containing the human IgG constant regions to form the intact human IgG molecule with the variable regions from the isolated bacteriophage specific for MAG.

The donor antibodies may contribute sequences, such as variable heavy and/or light chain peptide sequences, framework sequences, CDR sequences, functional fragments, and analogs thereof, and the nucleic acid sequences encoding them, useful in designing and obtaining various altered antibodies which are characterized by the antigen binding specificity of the donor antibody.

Taking into account the degeneracy of the genetic code, various coding sequences may be constructed which encode the variable heavy and light chain amino acid sequences, and CDR sequences as well as functional fragments and analogs thereof which share the antigen specificity of the donor antibody. Isolated nucleic acid sequences, or fragments thereof, encoding the variable chain peptide sequences or CDRs can be used to produce altered antibodies, e.g., chimeric or humanized antibodies, or other engineered antibodies when operatively combined with a second immunoglobulin partner.

Altered immunoglobulin molecules can encode altered antibodies which include engineered antibodies such as chimeric antibodies and humanized antibodies. A desired altered immunoglobulin coding region contains CDR-encoding regions that encode peptides having the antigen specificity of an anti-MAG antibody, preferably a high affinity antibody, inserted into a first immunoglobulin partner (a human framework or human immunoglobulin variable region).

Preferably, the first immunoglobulin partner is operatively linked to a second immunoglobulin partner. The second immunoglobulin partner is defined above, and may include a sequence encoding a second antibody region of interest, for example an Fc region. Second immunoglobulin partners may also include sequences encoding another immunoglobulin to which the light or heavy chain constant region is fused in frame or by means of a linker sequence. Engineered antibodies directed against functional fragments or analogs of MAG may be designed to elicit enhanced binding.

The second immunoglobulin partner may also be associated with effector agents as defined above, including non-protein carrier molecules, to which the second immunoglobulin partner may be operatively linked by conventional means.

Fusion or linkage between the second immunoglobulin partners, e.g., antibody sequences, and the effector agent may be by any suitable means, e.g., by conventional covalent or ionic bonds, protein fusions, or hetero-bifunctional cross-linkers, e.g., carbodiimide, glutaraldehyde, and the like. Such techniques are known in the art and readily described in conventional chemistry and biochemistry texts.

Additionally, conventional linker sequences which simply provide for a desired amount of space between the second immunoglobulin partner and the effector agent may also be constructed into the altered immunoglobulin coding region. The design of such linkers is well known to those of skill in the art. In further aspects of the invention we provide diabodies (bivalent or bispecific), triabodies, tetrabodies and other multivalent scFV protein species having one or more CDRs as described supra that bind to and neutralise MAG function.

In still a further embodiment, the antibody of the invention may have attached to it an additional agent. For example, the procedure of recombinant DNA technology may be used to produce an engineered antibody of the invention in which the Fc fragment or CH2-CH3 domain of a complete antibody molecule has been replaced by an enzyme or other detectable molecule (i.e., a polypeptide effector or reporter molecule).

The second immunoglobulin partner may also be operatively linked to a non-immunoglobulin peptide, protein or fragment thereof heterologous to the CDR-containing sequence having the antigen specificity of anti-MAG antibody. The resulting protein may exhibit both anti-MAG antigen specificity and characteristics of the non-immunoglobulin upon expression. That fusion partner characteristic may be, e.g., a functional characteristic such as another binding or receptor domain, or a therapeutic characteristic if the fusion partner is itself a therapeutic protein, or additional antigenic characteristics.

Another desirable protein of this invention may comprise a complete antibody molecule, having full length heavy and light chains, or any discrete fragment thereof, such as the Fab or F(ab')$_2$ fragments, a heavy chain dimer, or any minimal recombinant fragments thereof such as an F$_v$ or a single-chain antibody (SCA) or any other molecule with the same specificity as the selected donor mAb. Such protein may be used in the form of an altered antibody, or may be used in its unfused form.

Whenever the second immunoglobulin partner is derived from an antibody different from the donor antibody, e.g., any isotype or class of immunoglobulin framework or constant regions, an engineered antibody results. Engineered antibodies can comprise immunoglobulin (Ig) constant regions and variable framework regions from one source, e.g., the acceptor antibody, and one or more (preferably all) CDRs from the donor antibody. In addition, alterations, e.g., deletions, substitutions, or additions, of the acceptor mAb light and/or heavy variable domain framework region at the nucleic acid or amino acid levels, or the donor CDR regions may be made in order to retain donor antibody antigen binding specificity.

Such engineered antibodies are designed to employ one (or both) of the variable heavy and/or light chains of the anti-MAG mAb or one or more of the heavy or light chain CDRs. The engineered antibodies may be neutralising, as above defined.

Such engineered antibodies may include a humanized antibody containing the framework regions of a selected human immunoglobulin or subtype, or a chimeric antibody containing the human heavy and light chain constant regions fused to the anti-MAG antibody functional fragments. A suitable human (or other animal) acceptor antibody may be one selected from a conventional database, e.g., the KABAT® database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody.

Desirably the heterologous framework and constant regions are selected from human immunoglobulin classes and isotypes, such as IgG (subtypes 1 through 4), IgM, IgA, and IgE. However, the acceptor antibody need not comprise only human immunoglobulin protein sequences. For instance a gene may be constructed in which a DNA sequence encoding part of a human immunoglobulin chain is fused to a DNA sequence encoding a non-immunoglobulin amino acid sequence such as a polypeptide effector or reporter molecule.

Preferably, in a humanized antibody, the variable domains in both human heavy and light chains have been engineered by one or more CDR replacements. It is possible to use all six CDRs, or various combinations of less than the six CDRs. Preferably all six CDRs are replaced. It is possible to replace the CDRs only in the human heavy chain, using as light chain the unmodified light chain from the human acceptor antibody. Alternatively, a compatible light chain may be selected from another human antibody by recourse to the conventional antibody databases. The remainder of the engineered antibody may be derived from any suitable acceptor human immunoglobulin.

The engineered humanized antibody thus preferably has the structure of a natural human antibody or a fragment thereof, and possesses the combination of properties required for effective therapeutic use.

It will be understood by those skilled in the art that an engineered antibody may be further modified by changes in variable domain amino acids without necessarily affecting the specificity and high affinity of the donor antibody (i.e., an analog). It is anticipated that heavy and light chain amino acids may be substituted by other amino acids either in the variable domain frameworks or CDRs or both.

In addition, the constant region may be altered to enhance or decrease selective properties of the molecules of the instant invention. For example, dimerization, binding to Fc receptors, or the ability to bind and activate complement (see, e.g., Angal et al., *Mol. Immunol*, 30:105-108 (1993), Xu et al., *J. Biol. Chem*, 269:3469-3474 (1994), Winter et al., EP 307, 434-B).

An altered antibody which is a chimeric antibody differs from the humanized antibodies described above by providing the entire non-human donor antibody heavy chain and light chain variable regions, including framework regions, in association with immunoglobulin constant regions from other species, preferably human for both chains.

Preferably, the variable light and/or heavy chain sequences and the CDRs of suitable donor mAbs, and their encoding nucleic acid sequences, are utilized in the construction of altered antibodies, preferably humanized antibodies, of this invention, by the following process. The same or similar techniques may also be employed to generate other embodiments of this invention.

A hybridoma producing a selected donor mAb is conventionally cloned, and the DNA of its heavy and light chain variable regions obtained by techniques known to one of skill in the art, e.g., the techniques described in Sambrook et al., (*Molecular Cloning (A Laboratory Manual)*, 2nd edition, Cold Spring Harbor Laboratory (1989)). The variable heavy and light regions containing at least the CDR-encoding regions and those portions of the acceptor mAb light and/or heavy variable domain framework regions required in order to retain donor mAb binding specificity, as well as the remaining immunoglobulin-derived parts of the antibody chain derived from a human immunoglobulin are obtained using polynucleotide primers and reverse transcriptase. The CDR-encoding regions are identified using a known database and by comparison to other antibodies.

A mouse/human chimeric antibody may then be prepared and assayed for binding ability. Such a chimeric antibody contains the entire non-human donor antibody $V_H$ and $V_L$ regions, in association with human Ig constant regions for both chains.

Homologous framework regions of a heavy chain variable region from a human antibody may be identified using computerized databases, e.g., KABAT®, and a human antibody having homology to the donor antibody will be selected as the acceptor antibody. A suitable light chain variable framework region can be designed in a similar manner.

A humanized antibody may be derived from the chimeric antibody, or preferably, made synthetically by inserting the donor mAb CDR-encoding regions from the heavy and light chains appropriately within the selected heavy and light chain framework. Alternatively, a humanized antibody can be made using standard mutagenesis techniques. Thus, the resulting humanized antibody contains human framework regions and donor mAb CDR-encoding regions. There may be subsequent manipulation of framework residues. The resulting humanized antibody can be expressed in recombinant host cells, e.g., COS, CHO or myeloma cells.

A conventional expression vector or recombinant plasmid is produced by placing these coding sequences for the antibody in operative association with conventional regulatory control sequences capable of controlling the replication and expression in, and/or secretion from, a host cell. Regulatory sequences include promoter sequences, e.g., CMV promoter, and signal sequences, which can be derived from other known antibodies. Similarly, a second expression vector can be produced having a DNA sequence which encodes a complementary antibody light or heavy chain. Preferably this second expression vector is identical to the first except insofar as the coding sequences and selectable markers are concerned, so to ensure as far as possible that each polypeptide chain is functionally expressed. Alternatively, the heavy and light chain coding sequences for the altered antibody may reside on a single vector.

A selected host cell is co-transfected by conventional techniques with both the first and second vectors (or simply transfected by a single vector) to create the transfected host cell of the invention comprising both the recombinant or synthetic light and heavy chains. The transfected cell is then cultured by conventional techniques to produce the engineered antibody of the invention. The humanized antibody which includes the association of both the recombinant heavy chain and/or light chain is screened from culture by appropriate assay, such as ELISA or RIA. Similar conventional techniques may be employed to construct other altered antibodies and molecules.

Suitable vectors for the cloning and subcloning steps employed in the methods and construction of the compositions of this invention may be selected by one of skill in the art. For example, the conventional pUC series of cloning vectors, may be used. One vector, pUC19, is commercially available from supply houses, such as Amersham (Buckinghamshire, United Kingdom) or Pharmacia (Uppsala, Sweden). Additionally, any vector which is capable of replicating readily, has an abundance of cloning sites and selectable genes (e.g., antibiotic resistance), and is easily manipulated may be used for cloning. Thus, the selection of the cloning vector is not a limiting factor in this invention.

Similarly, the vectors employed for expression of the antibodies may be selected by one of skill in the art from any conventional vector. The vectors also contain selected regulatory sequences (such as CMV promoters) which direct the replication and expression of heterologous DNA sequences in selected host cells. These vectors contain the above described DNA sequences which code for the antibody or altered immunoglobulin coding region. In addition, the vectors may incorporate the selected immunoglobulin sequences modified by the insertion of desirable restriction sites for ready manipulation.

The expression vectors may also be characterized by genes suitable for amplifying expression of the heterologous DNA sequences, e.g., the mammalian dihydrofolate reductase gene (DHFR). Other preferable vector sequences include a poly A signal sequence, such as from bovine growth hormone (BGH) and the betaglobin promoter sequence (betaglopro). The expression vectors useful herein may be synthesized by techniques well known to those skilled in this art.

The components of such vectors, e.g. replicons, selection genes, enhancers, promoters, signal sequences and the like, may be obtained from commercial or natural sources or synthesized by known procedures for use in directing the expression and/or secretion of the product of the recombinant DNA in a selected host. Other appropriate expression vectors of which numerous types are known in the art for mammalian, bacterial, insect, yeast, and fungal expression may also be selected for this purpose.

The present invention also encompasses a cell line transfected with a recombinant plasmid containing the coding sequences of the antibodies or altered immunoglobulin molecules thereof. Host cells useful for the cloning and other manipulations of these cloning vectors are also conventional. However, most desirably, cells from various strains of E. coli are used for replication of the cloning vectors and other steps in the construction of altered antibodies of this invention.

Suitable host cells or cell lines for the expression of the antibody of the invention are preferably mammalian cells such as NS0, Sp2/0, CHO, COS, a fibroblast cell (e.g., 3T3), and myeloma cells, and more preferably a CHO or a myeloma cell. Human cells may be used, thus enabling the molecule to be modified with human glycosylation patterns. Alternatively, other eukaryotic cell lines may be employed. The selection of suitable mammalian host cells and methods for transformation, culture, amplification, screening and product production and purification are known in the art. See, e.g., Sambrook et al., cited above.

Bacterial cells may prove useful as host cells suitable for the expression of the recombinant Fabs of the present invention (see, e.g., Plückthun, A., *Immunol. Rev.*, 130: 151-188 (1992)). However, due to the tendency of proteins expressed in bacterial cells to be in an unfolded or improperly folded form or in a non-glycosylated form, any recombinant Fab produced in a bacterial cell would have to be screened for retention of antigen binding ability. If the molecule expressed by the bacterial cell was produced in a properly folded form, that bacterial cell would be a desirable host. For example, various strains of E. coli used for expression are well-known as host cells in the field of biotechnology. Various strains of B. subtilis, Streptomyces, other bacilli and the like may also be employed in this method.

Where desired, strains of yeast cells known to those skilled in the art are also available as host cells, as well as insect cells, e.g. Drosophila and Lepidoptera and viral expression systems. See, e.g. Miller et al., *Genetic Engineering*, 8:277-298, Plenum Press (1986) and references cited therein.

The general methods by which the vectors may be constructed, the transfection methods required to produce the host cells of the invention, and culture methods necessary to produce the altered antibody of the invention from such host cell are all conventional techniques. Likewise, once produced, the antibodies of the invention may be purified from the cell culture contents according to standard procedures of the art, including ammonium sulfate precipitation, affinity columns, column chromatography, gel electrophoresis and the like. Such techniques are within the skill of the art and do not limit this invention. For example, preparation of altered antibodies are described in WO 99/58679 and WO 96/16990.

Yet another method of expression of the antibodies may utilize expression in a transgenic animal, such as described in U.S. Pat. No. 4,873,316. This relates to an expression system using the animal's casein promoter which when transgenically incorporated into a mammal permits the female to produce the desired recombinant protein in its milk.

Once expressed by the desired method, the antibody is then examined for in vitro activity by use of an appropriate assay. Presently conventional ELISA assay formats are employed to assess qualitative and quantitative binding of the antibody to MAG. Additionally, other in vitro assays may also be used to verify neutralizing efficacy prior to subsequent human clinical studies performed to evaluate the persistence of the antibody in the body despite the usual clearance mechanisms.

The therapeutic agents of this invention may be administered as a prophylactic or post injury, or as otherwise needed. The dose and duration of treatment relates to the relative duration of the molecules of the present invention in the human circulation, and can be adjusted by one of skill in the art depending upon the condition being treated and the general health of the patient.

The mode of administration of the therapeutic agent of the invention may be any suitable route which delivers the agent to the host. The antagonists and antibodies, and pharmaceutical compositions of the invention are particularly useful for parenteral administration, i.e., subcutaneously, intramuscularly, intravenously, or intranasally.

Therapeutic agents of the invention may be prepared as pharmaceutical compositions containing an effective amount of the antagonist or antibody of the invention as an active ingredient in a pharmaceutically acceptable carrier. In the prophylactic agent of the invention, an aqueous suspension or solution containing the engineered antibody, preferably buffered at physiological pH, in a form ready for injection is preferred. The compositions for parenteral administration will commonly comprise a solution of the antagonist or antibody of the invention or a cocktail thereof dissolved in an pharmaceutically acceptable carrier, preferably an aqueous carrier. A variety of aqueous carriers may be employed, e.g., 0.9% saline, 0.3% glycine, and the like. These solutions are sterile and generally free of particulate matter. These solutions may be sterilized by conventional, well known sterilization techniques (e.g., filtration). The compositions may contain pharmaceutically acceptable auxiliary substances as required to approximate physiological conditions such as pH adjusting and buffering agents, etc. The concentration of the antagonist or antibody of the invention in such pharmaceutical formulation can vary widely, i.e., from less than about 0.5%, usually at or at least about 1% to as much as 15 or 20% by weight and will be selected primarily based on fluid volumes, viscosities, etc., according to the particular mode of administration selected.

Thus, a pharmaceutical composition of the invention for intramuscular injection could be prepared to contain 1 mL sterile buffered water, and between about 1 ng to about 100 mg, e.g. about 50 ng to about 30 mg or more preferably, about 5 mg to about 25 mg, of an antagonist or antibody of the invention. Similarly, a pharmaceutical composition of the invention for intravenous infusion could be made up to contain about 250 ml of sterile Ringer's solution, and about 1 to about 30 and preferably 5 mg to about 25 mg of an engineered antibody of the invention. Actual methods for preparing parenterally administrable compositions are well known or will be apparent to those skilled in the art and are described in more detail in, for example, Remington's Pharmaceutical Science, 15th ed., Mack Publishing Company, Easton, Pa.

It is preferred that the therapeutic agent of the invention, when in a pharmaceutical preparation, be present in unit dose forms. The appropriate therapeutically effective dose can be determined readily by those of skill in the art. To effectively treat stroke and other neurological diseases in a human, one dose of up to 700 mg per 70 kg body weight of an antagonist or antibody of this invention should be administered parenterally, preferably i.v. or i.m. (intramuscularly). Such dose may, if necessary, be repeated at appropriate time intervals selected as appropriate by a physician.

The antibodies described herein can be lyophilized for storage and reconstituted in a suitable carrier prior to use. This technique has been shown to be effective with conventional immunoglobulins and art-known lyophilization and reconstitution techniques can be employed.

In another aspect, the invention provides a pharmaceutical composition comprising anti-MAG antibody of the present invention or a functional fragment thereof and a pharmaceutically acceptable carrier for treatment or prophylaxis of stroke and other neurological diseases.

In a yet further aspect, the invention provides a pharmaceutical composition comprising the anti-MAG antibody of the present invention or a functional fragment thereof and a pharmaceutically acceptable carrier for inhibiting neurodegeneration and/or promoting functional recovery in a human patient suffering, or at risk of developing, a stroke or other neurological disease.

The following examples illustrate the invention.

EXAMPLE 1

Anti-MAG Antibody in Stroke Model

Materials and Methods
Anti-MAG Monoclonal Antibody

Anti-MAG monoclonal antibody was mouse anti-chick MAG antibody MAB 1567 obtained from Chemicon. The antibody has the following characteristics:

Antigen: myelin-associated glycoprotein (human, mouse, rat, bovine, chick, frog)

Isotype: IgG1

Neutralising ability: see DeBellard et al (1996) *Mol. Cell. Neurosci.* 7, 89-101; Tang et al (1997) *Mol. Cell Neurosci.* 9, 333-346; Torigoe K and Lundborg G (1997) *Exp. Neurology* 150, 254-262.

Control IgG1 mab was purchased from R+D Systems.
Intra-Cerebral Ventricular Cannulation (for Study 1 Only)

Under halothane anaesthesia intra-cerebral ventricular (i.c.v.) cannulae were positioned in the left lateral cerebral ventricle (coordinates: 1.6 mm from the midline, 0.8 mm caudal from bregma, 4.1 mm from skull surface, incisor bar −3.2 mm below zero according to Paxinos and Watson, 1986) All rats were singly housed to avoid damage to the guide or dummy cannula. 7 days following surgery, correct cannula placement was verified by an intense drinking response to Angiotensin II (100 ng, Simpson, et al. 1978). Nine days later, animals underwent cerebral ischaemia.

Transient Focal Cerebral Ischaemia

Transient (90 min) focal cerebral ischaemia was induced in male Sprague Dawley rats, each weighing between 300-350 g. The animals were initially anaesthetised with a mixture of 5% halothane, 60% nitrous oxide and 30% oxygen, placed on a facemask and anaesthesia subsequently maintained at 1.5% halothane. Middle cerebral artery occlusion (MCAO) was carried out using the intraluminal thread technique as described previously (Zea Longa, et. al., 1989). Animals were maintained normothermic throughout the surgical procedure, allowed to recover for 1 h in an incubator, before being singly housed. Only those animals with a neurological score of 3 1h post-occlusion were included in the study (as assessed using a 5-point scoring system: 0, no deficit; 1, contralateral reflex; 2, weakened grip; 3, circling; 4, immobile; 5, dead). Animals were maintained for up to 1 week at which time animals were killed by transcardial perfusion of 0.9% saline followed by 4% paraformaldehyde in 100 mM phosphate buffer. The brains were post-fixed in 4% paraformaldehyde at 4° C. for 48 h at which time they were removed from the skulls and cut into 2 mm blocks using a rat brain matrix. The 2 mm sections were then paraffin embedded using a Shandon Citadel 1000 tissue processor, cut into 6 µm sections using a microtome and mounted on poly-L-lysine coated slides. Sections were then processed for Cresyl Fast Violet (CFV) staining.

Dosing Regime

Anti-MAG monoclonal antibody and mouse IgG1 isotype control antibody were dialysed against sterile 0.9% sodium chloride overnight and concentrated appropriately.

Study 1: Animals received 2.5 µg of anti-MAGmab or 2.5 µg mouse IgG i.c.v. 1, 24 and 72 h following MCAO (5 ul per dose).

Study 2: Animals received 200 µg of anti-MAG mab or 200 µg mouse IgG i.v. 1 and 24 following MCAO.

Investigator was blinded to the identity of each dosing solution.

Neurological Assessment

Prior to induction of cerebral ischaemia, rats for Study 1 received training in beam walking and sticky label test. Animals not reaching criteria in both tests were excluded from further study. Following training, the remainder of the animals were stratified according to performance into two balanced groups. Throughout the neurological assessment, the investigators were blinded to the treatment group of the animal.

Bilateral Sticky Label Test

The bilateral sticky label test (Schallert et al., *Pharmacology Biochemistry and Behaviour* 16: 455-462, (1983)) was used to assess contralateral neglect/ipsilateral bias. This models tactile extinction observed in human stroke patients (Rose, et al. 1994). This test has been described in detail previously (Hunter, et al., *Neuropharmacology* 39: 806-816 (2000); Virley et al *Journal of Cerebral Blood Flow & Metabolism,* 20: 563-582 (2000)). Briefly, a round, sticky paper label was placed firmly around the hairless area of the forepaws with equal pressure with order of placement randomised (left, right). Training sessions were conducted for 6 days prior to MCAO, day 6 data was utilised as the pre-operative baseline (Day 0). Animals were given two trials 24 and 7 d following MCAO, the data represents a mean of the two trials. The latency to contact and remove the labels were recorded and analysed using the logrank test (Cox, *J. Royal Statistical Society B* 34: 187-220 (1972)).

Beam Walking

Beam walking was used as a measure of hind-limb and fore-limb co-ordination by means of distance travelled across an elevated 100 cm beam (2.3 cm diameter, 48 cm off the floor) as previously described in detail (Virley et al *Journal of Cerebral Blood Flow & Metabolism,* 20: 563-582 (2000)). Rats were trained to cross the beam from start to finish. For testing, each rat was given 2 trials 24 h and 7 d following MCAO, the data represents a mean of the two trials. Statistical analysis was ANOVA followed by Student's t-test.

The 27-Point Neurological Score (Study-1)

This study consists of a battery of tests to assess neurological status including, paw placement, visual forepaw reaching, horizontal bar, contralateral rotation, inclined plane, righting reflex, contralateral reflex, motility & general condition, as described previously (Hunter, et al. *Neuropharmacology* 39: 806-816 (2000)) with the addition of grip strength measurements (scores 2 for good right fore-limb grip, 1 for weak grip). Total score=27 for normal animal.

For study 2 this test was modified further: Grip strength—normal scores 3, good—2, weak—1, very weak—0; Motility—normal scores 4, excellent—3, very good—2, good—1, fair—0; General Condition—normal scores 4, excellent—3, very good—2, good—1, fair—0; Circling—none scores 5, favours one-side scores 4, large circle—3, medium circlep—2, small circle—1, spinning—0). Total score=32 for a normal animal.

In both studies animals were tested 1, 24, 48 h and 7 d following MCAO, a healthy normal animal scores 27 or 32 respectively. Data are presented as median values, Statistical analysis was Kruskil Wallis ANOVA.

Lesion Assessment

Study 1—For each animal, lesion areas were assessed in sections from three pre-determined levels in the brain (0, −2.0 and −6.0 mm from Bregma respectively). Neuronal damage was assessed using cresyl fast violet staining and the area of damage measured using an Optimas 6.1 imaging package. Data is expressed as mean area ($mm^2$)±sem. Study 2—For each animal, lesion areas were assessed in sections from seven pre-determined levels in the brain (+3 mm to −8 mm w.r.t. Bregma). Neuronal damage was assessed using cresyl fast violet staining and the area of damage measured using an Optimas 6.1 imaging package. Data is expressed as mean area ($mm^2$)±sem.

Results

Study 1—Intra-Cerebral Ventrical (i.c.v.) Administration of Anti-MAG Mab

Neurological Score

One hour following MCAO animals in both treatment groups showed marked impairment in neurological score (median score 12 in each group). There was no significant difference between groups at this time. However, 24 ($p=0.02$), 48 ($p=0.005$) h and 7 d ($p=0.006$) following MCAO animals treated with anti-MAG mab (2.5 µg, 1, 24 and 72 h post-MCAO) showed significantly improved Total Neurological score compared to those treated with control IgG. Median neurological scores 24, 48 h and 7 d following MCAO in the $IgG_1$ treated group were 15, 14 and 18 respectively compared to 19.5, 21.5 and 22 in the anti-MAG mab treated animals. On further analysis of the individual behaviours comprising the total score, this significant improvement was mainly attributed to improved performance in the following tests: paw placement (24 h, $p=0.045$; 48 h, $p=0.016$; 7 d, $p=0.008$), grip strength (24 h, $p=0.049$ 48 h, $p=0.0495$; 7 d, $p=0.243$), motility (24 h, $p=0.199$; 48 h, $p=0.012$; 7 d, p=0.067), horizontal bar (24 h, p=0.065; 48 h, p=0.005; 7 d, p=0.016), inclined plane (24 h, p=0.006; 48 h, p=0.006; 7 d, p=0.169), visual forepaw reaching (48 h, p=0.049, 7 d, p=0.049) and the degree of circling (24 h, p=0.417; 48 h, p=0.034; 7 d, p=0.183).

Beam Walking

Prior to surgery all animals were trained to cross the beam (100 cm). Twenty four hours following surgery there was a significant impairment on the distance travelled on the beam in both anti-MAG (50±18 cm) and IgG$_1$ (22±14 cm) treated animals compared to pre-operative values. Although not significant, anti-MAG treated animals showed marked improvement over IgG$_1$ treated animals in that they travelled twice the distance of IgG$_1$ treated animals 24 h following tMCAO. Seven days following surgery however, while both groups showed marked improvement over time, the performance of animals treated with IgG remained significantly impaired compared to baseline (55±15 cm; p=0.005). In contrast however 7 d following MCAO, animals treated with anti-MAG mab (2.5 μg 1, 24 and 72 h, i.c.v post MCAO) performance was not significantly different from baseline (75±15 cm; p=0.07). This data shows that anti-MAG mab treatment accelerated recovery of this beam walking task compared to mouse IgG$_1$ treated controls.

Sticky Label

Prior to surgery, animals in each of the treatment groups rapidly contacted and removed the labels from each forepaw, there was no significant difference in the groups prior to treatment (Table 1). Twenty-four hours and 7 d following MCAO the latency to contact the left paw in each of the treatment groups remained relatively unaltered, while that of the right was markedly increased. However there was no significant differences between removal times in anti-MAG and IgG$_1$ treated animals. In addition 24 h following MCAO, the latency to removal from both the left and right forepaw was significantly increased in both treatment groups compared to baseline, however in anti-MAG treated animals the latency to removal from the left paw was significantly shorter than that of IgG$_1$ treated animals (p=0.03). There was also a trend for reduced latency to removal from the right paw in anti-MAG treated animals compared to those treated with IgG$_1$ (p=0.08) (Table 1). At 7 d there was some degree of recovery in IgG$_1$ treated animals in that the latency to removal times for each forepaw were reduced compared to those at 24 h (Table 1). This data suggests that treatment of rats with anti-MAG mab accelerate the recovery in this sticky label test following tMCAO.

TABLE 1

Sticky label data

| | | Contact Time (s) (Mean ± sem) | | Removal Time (s) (Mean ± sem) | |
|---|---|---|---|---|---|
| Day | Treatment | Left Forepaw | Right Forepaw | Left Forepaw | Right Forepaw |
| 0 | Anti-MAG | 2.4 ± 0.2 | 3.6 ± 0.5 | 12 ± 2 | 12 ± 2 |
| 0 | IgG$_1$ | 3.3 ± 0.6 | 4.2 ± 0.7 | 10 ± 1 | 9 ± 1 |
| 1 | Anti-MAG | 5.9 ± 3.7 | 109.6 ± 27.5 | *61 ± 26 | 96 ± 26 |
| 1 | IgG$_1$ | 3.6 ± 0.5 | 71.8 ± 31.7 | 130 ± 21 | 156 ± 19 |
| 7 | Anti-MAG | 3.8 ± 1 | 36.4 ± 10.2 | 54 ± 23 | 80 ± 30 |
| 7 | IgG$_1$ | 2.8 ± 0.3 | 64 ± 28 | 23 ± 8 | 87 ± 20 |

(*p = 0.03 Anti-MAG v's IgG$_1$ using the logrank test)

Lesion Area Measurements

Administration of anti-MAG mab i.c.v, significantly reduced lesion area in two of the three brain levels examined compared to those animals treated with equal amounts of mouse IgG$_1$ when examined 7 days following tMCAO (Table 2).

TABLE 2

Mean Lesion Area ± sem (mm$^2$) 7 d following tMCAO

| Treatment | 0 mm wrt Bregma | −2 mm wrt Bregma | −6 mm wrt Bregma |
|---|---|---|---|
| Anti-MAG mab (n = 8) | *9 ± 2 | $4 ± 3 | #3 ± 1 |
| Mouse IgG$_1$ (n = 9) | 14 ± 1 | 12 ± 1 | 5 ± 1 |

(*p = 0.02,
$p = 0.03,
p = 0.06, anti-MAG v's IgG$_1$, One-way, unpaired Students T-Test)

Study 2—Intra-Venous (i.v.) Administration

Neurological Score

One and 24 hours following MCAO animals in both groups showed marked impairment in neurological score. There was no significant difference between groups at this time, median scores 24 h following anti-MAG mab and IgG$_1$ treatment were 20 and 18 respectively (p=0.5). Forty-eight hours following MCAO, animals treated with anti-MAG mab (200 ug, i.v. 1 and 24 h post-MCAO) showed significant improvement in paw placement (p=0.048) and grip strength (p=0.033). Seven days following the onset of cerebral ischaemia animals treated with anti-MAG mab continued to improve (paw placement p=0.041; grip strength, p=0.048; motility, p=0.05) and showed significant improvement in total neurological score (median score 25) compared to those treated with mouse IgG$_1$ (Median score 23, p=0.047).

Lesion Area Measurements

The anti-MAG antibody when administered i.v. MCAO significantly reduced lesion area at 5 out of 7 pre-determined brain levels (+3 to −8 mm w.r.t. Bregma) compared to isotype controls, when examined 7 d following MCAO.

| Brain level wrt Bregma | Mean lesion area ± SEM (mm$^2$) - Anti- MAG treated | Mean lesion area ± SEM (mm$^2$) - Mouse IgG$_1$ treated |
|---|---|---|
| 3 mm | *0.38 ± 0.27 | 1.77 ± 0.45 |
| 1 mm | *5.82 ± 1.65 | 9.627 ± 1.14 |
| −1 mm | 8.98 ± 2.58 | 12.07 ± 1.57 |
| −2 mm | 7.28 ± 1.92 | 10.04 ± 1.87 |
| −4 mm | *5.57 ± 1.06 | 10.38 ± 1.39 |
| −6 mm | *1.36 ± 0.51 | 4.43 ± 1.95 |
| −8 mm | *0.27 ± 0.27 | 1.93 ± 0.56 |

*p < 0.05 - Unpaired, one-way Students T-test

Conclusions

An anti-MAG monoclonal antibody administered either directly into the CSF or intravenously following transient middle-cerebral artery occlusion in the rat, both reduced the area of cell death and improved functional recovery compared to control treated animals. The degree of neuroprotection seen in these studies suggests that this effect can not be attributed to axonal sprouting as this would not result in neuronal sparing. The improvement in functional recovery seen 24 and 48 h following MCAO probably reflects the degree of neuroprotection offered by this antibody compared to control treated animals. However, over time the animals appear to improve further, suggesting that blocking MAG activity can also enhance functional recovery over time.

The studies presented here provide evidence that blocking the actions of MAG provide both neuroprotection and enhanced functional recovery in a rat model of stroke, and therefore anti-MAG antibodies provide potential therapeutic agents for acute neuroprotection and/or the promotion of functional recovery following stroke. The low amounts of antibody administered via the i.v route and the resulting low serum levels of the antibody would in turn suggest extremely low antibody concentrations in the brain due to the constraints of the blood brain barrier for antibody penetration. Surprisingly, however, this still resulted in both, neuroprotection and enhanced functional recovery being observed. Anti-MAG antibodies also have potential use in the treatment of other neurological disorders where the degeneration of cells and or nerve fibres is apparent such as spinal cord injury, traumatic brain injury, peripheral neuropathy, Alzheimer's disease, fronto-temporal dementias (tauopathies), Parkinson's disease, Huntington's disease and Multiple Sclerosis. In the examples that follow the CDRs of the chimeric and humanised antibodies disclosed therein are the CDRs of the antibody of example 1.

EXAMPLE 2

Chimeric Antibody

Altered antibodies include chimeric antibodies which comprise variable regions deriving from one species linked to constant regions from another species. Examples of mouse-human chimeric anti-MAG immunoglobulin chains of the invention are provided in FIGS. 1, 2, and 3. Mouse-human chimeras using human IgG1, IgG2, IgG3, IgG4, IgA, IgE, IgM, IgD constant regions may be produced, as may chimeras associating the mouse variable regions with heavy or light chain constant regions from non-human species.

FIG. 1 (Seq ID No. 27) provides the amino acid sequence of a chimeric immunoglobulin heavy chain in which the murine anti-MAG heavy chain variable region is associated with a functional immunoglobulin secretion signal sequence, and with an altered form of the human IgG1 constant region, in which Kabat residues 248 and 250 have been mutated to alanine in order to disable the effector functions of binding to FcγRI and complement protein C1q (Duncan, A. R. and Winter, G. Localization of the C1q binding site on antibodies by surface scanning. Nature 332, 738-740, 1988. Duncan, A. R., Woolf, J. M., Partridge, L. J., Burton, D. R. and Winter, G. Localisation of the binding site for human FcR1 on IgG. Nature 332, 563-564, 1988). Such mutations are optionally made in order to customise the properties of an altered antibody to achieve a particular therapeutic effect—for example binding to and blocking the function of an antigen without activating lytic effector mechanisms.

FIG. 2 (Seq ID No. 28) provides the amino acid sequence of a chimeric immunoglobulin light chain in which the murine anti-MAG light chain variable region is associated with a functional immunoglobulin secretion signal sequence, and with the human kappa constant region.

Similarly, the anti-MAG variable regions may be associated with immunoglobulin constant regions which lack mutations disabling effector functions. FIG. 3 (Seq ID No. 29) provides the amino acid sequence of a chimeric immunoglobulin heavy chain in which the murine anti-MAG heavy chain variable region is associated with a functional immunoglobulin secretion signal sequence, and with a wild-type form of the human IgG1 constant region.

From the information provided in FIGS. 1 to 3, cDNA inserts encoding these chimeric chains may be prepared by standard molecular biology techniques well known to those skilled in the art. Briefly, the genetic code is used to identify nucleotide codons encoding the desired amino acids, creating a virtual cDNA sequence encoding the chimeric protein. If the cDNA insert is desired to be expressed in a particular organism, then particularly favoured codons may be selected according to known codon usage biases. The desired nucleotide sequence is then synthesised by means of PCR amplification of a template comprising overlapping synthetic oligonucleotides which, as a contig, represent the desired sequence. The resulting product may also be modified by PCR or mutagenesis to attach restriction sites to facilitate cloning into a suitable plasmid for expression or further manipulations.

EXAMPLE 3

Chimeric Antibody Binds to Rat MAG in ELISA

Chimeric anti-MAG antibody containing the light and heavy chain CDRs of the invention was produced by transient transfection of CHO cells. For this, Transfast transfection reagent (Promega; E2431) was used and transfections carried out according to manufactures instructions. In brief, ~$10^6$ CHO cells were plated out per well of 6-well culture plates. The following day mammalian expression vector DNA encoding the appropriate heavy or light chain were mixed at 1:1 ratio (5 μg total DNA) in medium (Optimem1 with Glutamax; Gibco #51985-026). Transfast transfection reagent was added and the solution transferred to wells with confluent cell layers. After 1 h at 37° C. in the cell incubator, the DNA/Transfast mixture was overlaid with 2 ml Optimem medium and left for 48-72 h in the incubator. Supernatants were harvested, cleared by centrifugation and passed through 0.2 μm filters. Antibody concentration in CHO cell culture supernatant was determined by ELISA and estimated to be around 0.5 μg/ml. For MAG binding, commercially available ratMAG-Fc was used. Due to the fusion with human Fc bound chimeric antibodies could not be detected using anti-human IgG secondary antibodies. Instead, anti-human kappa light chain-specific antibody was used. FIG. 4 shows that this chimeric antibody binds to MAG even at 1/64 dilution. An unrelated humanised antibody and culture supernatant from mock transfected cells did not generate any signal in this assay.

Procedure:

ELISA microtiter plates (Nunc Maxisorp) were coated with 1 μg/ml rat MAG-Fc fusion protein (R&D systems; 538-MG) in PBS at 4° C. overnight. Plates were washed twice with PBS and then blocked with PBS/BSA (1% w/v) for 1 h at room temperature (RT). Culture supernatants from transiently transfected CHO cells were passed through 0.2 μm filters and serial diluted in PBS/BSA starting at neat supernatant to 1/64 dilution. Sample dilutions were left at RT for 1 h. Plates were then washed three times with PBS/Tween 20 (0.1% v/v). Detection antibody was goat anti-human kappa light chain specific-peroxidase conjugate (Sigma A-7164) diluted at 1/2000 in PBS/BSA. The detection antibody was incubated for 1 h at RT and the plates washed as above. Substrate solution (Sigma Fast OPD P-9187) was added and incubated until appropriate colour development was detected and then stopped using 3M $H_2SO_4$. Colour development was read at 490 nm.

EXAMPLE 4

Humanised Antibodies

Altered antibodies include humanised antibodies which comprise humanised variable regions linked to human constant regions. Examples of humanised anti-MAG immunoglobulin chains of the invention are provided in FIG. 5. Humanised antibodies using human IgG1, IgG2, IgG3, IgG4, IgA, IgE, IgM, IgD constant regions may be produced.

FIG. 5 (Seq ID No: 30) provides an example of the amino acid sequence of a humanised immunoglobulin heavy chain in which the humanised anti-MAG heavy chain variable region is associated with a functional immunoglobulin secretion signal sequence, and with an altered form of the human IgG1 constant region, in which Kabat residues 248 and 250 have been mutated to alanine in order to disable the effector functions of binding to FcγRI and complement protein C1q (Duncan, A. R. and Winter, G. Localization of the C1q binding site on antibodies by surface scanning. Nature 332, 738-740, 1988. Duncan, A. R., Woolf, J. M., Partridge, L. J., Burton, D. R. and Winter, G. Localisation of the binding site for human FcR1 on IgG. Nature 332, 563-564, 1988). Such mutations are optionally made in order to customise the properties of an altered antibody to achieve a particular therapeutic effect—for example binding to and blocking the function of an antigen without activating lytic effector mechanisms.

FIG. 5 (Seq ID No. 31) also provides an example of the amino acid sequence of a humanised immunoglobulin light chain in which the humanised anti-MAG light chain variable region is associated with a functional immunoglobulin secretion signal sequence, and with the human kappa constant region.

Similarly, the anti-MAG variable regions may be associated with immunoglobulin constant regions which lack mutations disabling effector functions. FIG. 5 (Seq ID No. 32) provides the amino acid sequence of a humanised immunoglobulin heavy chain in which the humanised anti-MAG heavy chain variable region is associated with a functional immunoglobulin secretion signal sequence, and with a wild-type form of the human IgG1 constant region.

From the information provided in FIG. 5, cDNA inserts encoding these humanised chains may be prepared by standard molecular biology techniques well known to those skilled in the art. Briefly, the genetic code is used to identify nucleotide codons encoding the desired amino acids, creating a virtual cDNA sequence encoding the protein. If the cDNA insert is desired to be expressed in a particular organism, then particularly favoured codons may be selected according to known codon usage biases. The desired nucleotide sequence is then synthesised by means of PCR amplification of a template comprising overlapping synthetic oligonucleotides which, as a contig, represent the desired sequence. The resulting product may also be modified by PCR or mutagenesis to attach restriction sites to facilitate cloning into a suitable plasmid for expression or further manipulations.

EXAMPLE 5

Humanised Anti-MAG Antibodies Bind to Rat and Human MAG in Elisa

1) Direct Binding ELISA to Rat MAG-Fc Fusion Protein of Normalised Amounts of Culture Supernatant for 9 Humanised Heavy and Light Chain Combinations Humanised anti-MAG antibodies containing the light and heavy chain CDRs of the invention were produced by transient transfection of CHO cells. For this, Transfast transfection reagent (Promega; E2431) was used and transfections carried out according to manufactures instructions. In brief, ~$10^6$ CHO cells were plated out per well of 6-well culture plates. The following day mammalian expression vector DNA encoding the appropriate heavy or light chain were mixed at 1:1 ratio (5 μg total DNA) in medium (Optimem1 with Glutamax; Gibco #51985-026). Transfast transfection reagent was added and the solution transferred to wells with confluent cell layers. After 1 h at 37° C. in the cell incubator, the DNA/Transfast mixture was overlaid with 2 ml Optimem medium and left for 48-72 h in the incubator. Supernatants were harvested, cleared by centrifugation and passed through 0.2 μm filters. 9 heavy and light variable chain combinations were produced from the sequences shown in the table below and the IgG1 heavy chain constant regions were functional according to Seq.ID.

| Seq ID No (V-regions) | Description | Alternative name |
|---|---|---|
| 13 | Humanised Vh | BVh1 |
| 14 | Humanised Vh | BVh2 |
| 15 | Humanised Vh | BVh3 |
| 16 | Humanised Vl | CVl1 |
| 17 | Humanised Vl | CVl2 |
| 18 | Humanised Vl | CVl3 |
| 19 | Humanised Vl | CVl4 |

Figure 6:
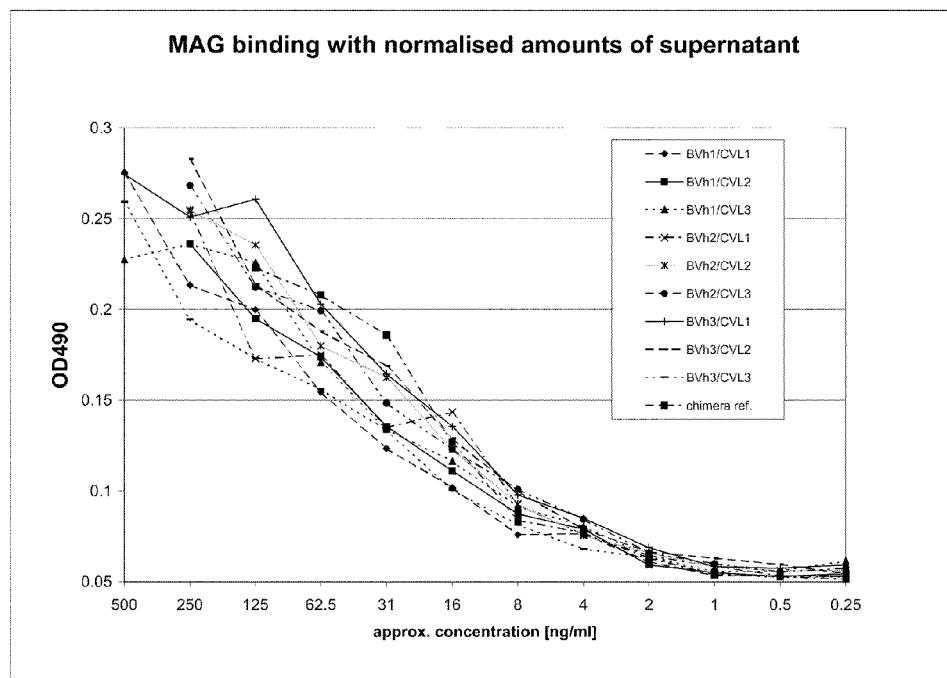
FIG. 6: Humanised anti-MAG antibodies bind to rat MAG

Antibody concentration was determined by ELISA and the amounts of supernatant used in the assay normalised to a starting concentration of 250 or 500 ng/ml (depending on concentration of culture supernatant). As antigen, commercially available ratMAG-Fc was used (R&D Systems; 538-MG). Due to the fusion of this antigen with human Fc, bound chimeric antibodies could not be detected using general anti-human IgG secondary antibodies. Instead, anti-human kappa light chain-specific antibody was used. FIG. 6 shows that all 9 humanised antibodies examined here bound to rat MAG with very similar binding curves down to ~4 ng/ml. The chimeric antibody used as a reference showed binding characteristics that fell within the group of humanised antibodies examined here. Although not absolute, this may suggest that the affinities of the humanised antibodies examined here lie very closely within the affinity range of the non-humanised chimeric antibody used as a reference here.

Procedure 96-well Nunc Maxisorp plates were coated overnight at 4° C. with rat MAG-Fc fusion protein (1 μg/ml; R&D Systems; Cat.No. 538-MG) in PBS. Plates were washed twice with PBS containing Tween20 (0.1% v/v; PBST) and blocked with PBS containing BSA (1% w/v) for 1 h at room temperature (RT). Variable amounts of culture supernatants were serial diluted in blocking buffer and added to the blocked wells starting at approximately 500 or 250 ng/ml. Antibody concentrations of supernatants were based on independent assays measuring the amount of humanised antibody present in each culture supernatant. Chimeric mouse-human (non-humanised) antibody was also included as reference. Antibody samples were incubated 1 h at RT and plates then washed 3× with PBST. Secondary antibody (Goat anti-human light chain specific-peroxidase conjugate; Sigma A-7164) was added diluted 1/5000 in blocking buffer and incubated for 1 h at RT. Wells were washed three times as above and binding detected by adding substrate (OPD tablets dissolved according to instructions; Sigma P-9187). Colour development was monitored and the reaction stopped using 3M H$_2$SO$_4$. Colour development was read at 490 nm.

Figure 7:
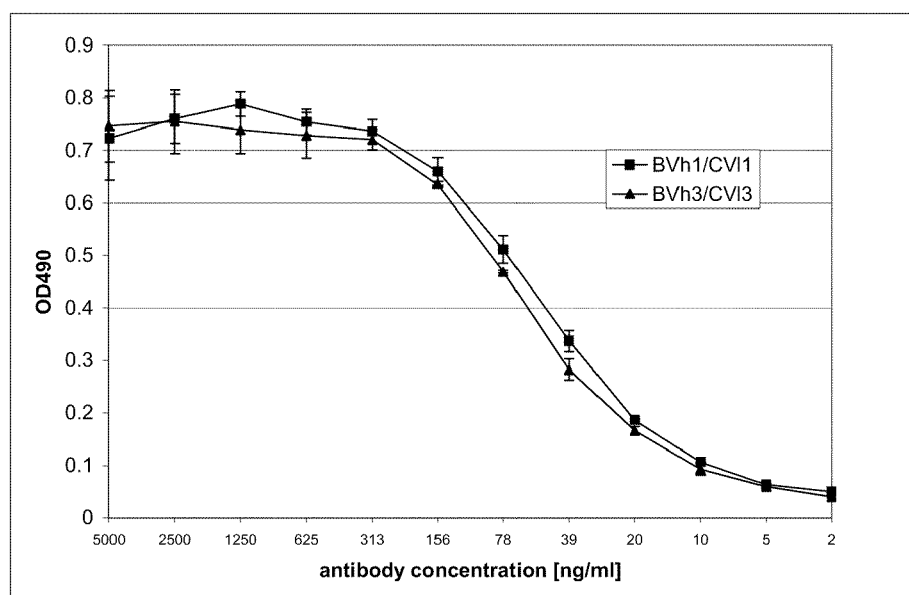
FIG. 7: Humanised anti-MAG antibodies bind to rat MAG

2) Direct Binding ELISA to Rat MAG-Fc Fusion Protein of Two Purified Humanised Anti-MAG Antibody Heavy-Light Chain Combinations Two humanised antibodies consisting of heavy and light chain variable region combinations BVh1/CVl1 and BVh3/CVl3 (table FIG. 5) and a mutated IgG1 constant region as exemplified by SEQ.I.D.NO:30 (which is BVh1/CVl1 mutated IgG1, those skilled in the art can readily derive the sequence for the BVh3/CVl3 equivalent) were produced by a scaled-up version of the transient transfection described in example 3 and purified using protein A affinity chromatography. Purified antibody material was dialysed against PBS and the concentration determined by OD280 reading. Antibody concentrations were adjusted to 5000 ng/ml and used as serial dilutions in a rat MAG-Fc binding ELISA. FIG. 7 shows that purified antibody material binds rat MAG-Fc and that both heavy and light chain variable region combinations tested here are extremely similar.

Method 96-well Nunc Maxisorp plates were coated overnight at 4° C. with rat MAG-Fc fusion protein (2.5 µg/ml; R&D Systems; Cat. No. 538-MG) in PBS. Plates were washed twice with PBS containing Tween20 (0.1% v/v; PBST) and blocked with PBS containing BSA (1% w/v) for 1 h at room temperature (RT). Purified humanised antibody was adjusted to a starting concentration of 5 µg/ml in blocking buffer and then serial diluted. Antibody samples were incubated 1 h at RT and plates then washed 3× with PBST. Secondary antibody (Goat anti-human light chain specific-peroxidase conjugate; Sigma A-7164) was added diluted 1/5000 in blocking buffer and incubated for 1 h at RT. Wells were washed three times as above and binding detected by adding substrate (OPD tablets dissolved according to instructions; Sigma P-9187). Colour development was monitored and the reaction stopped using 3M H$_2$SO$_4$. Colour development was read at 490 nm.

Results

Both purified humanised antibodies carrying none or several framework mutations show extremely similar binding to rat MAG. The results are seen in FIG. 7.

3) Binding to Human MAG Expressed on CHO Cells of Normalised Amounts of Culture Supernatant for Two Humanised Heavy and Light Chain Combinations The same humanised variable heavy and light chain combinations described in example 5 2) were tested as cleared culture supernatants against human MAG expressed on the surface of CHO cells. The amount of culture supernatant used for each antibody was normalised based on antibody concentrations determined by ELISA. For this, 96-well plates (Nunc Maxisorp) were coated overnight at 4° C. with goat anti-human IgG (gamma) chain (Sigma I-3382; in bicarbonate buffer pH9.6; 2 µg/ml). Following day, plates were washed twice with wash buffer (PBST) and blocked by adding at least 75 µl blocking buffer (PBS containing BSA 1% w/v) for 1 h at RT. Antibody sample solution were serial diluted in blocking buffer (starting dilution neat or ½) in duplicate. Ab standard was purified humanised IgG1 antibody of an unrelated specificity and known concentration. The standard solution was also serial diluted across plate starting at 500 ng/ml. All antibody solutions were incubated for 1 h at RT. Plates were washed 3× as above and then incubated with goat anti-human light (kappa) chain specific (free and bound) peroxidase conjugate (Sigma; A-7164) at 1/5000 in blocking buffer for 1 h@RT. Plates were again washed 3× as above and incubated with substrate solution (OPD tablets; Sigma P-9187 until strong colour development. Colour development was stopped by adding 25 µl 3M H2SO4 and the plate read at 490 nm.

Figure 8:
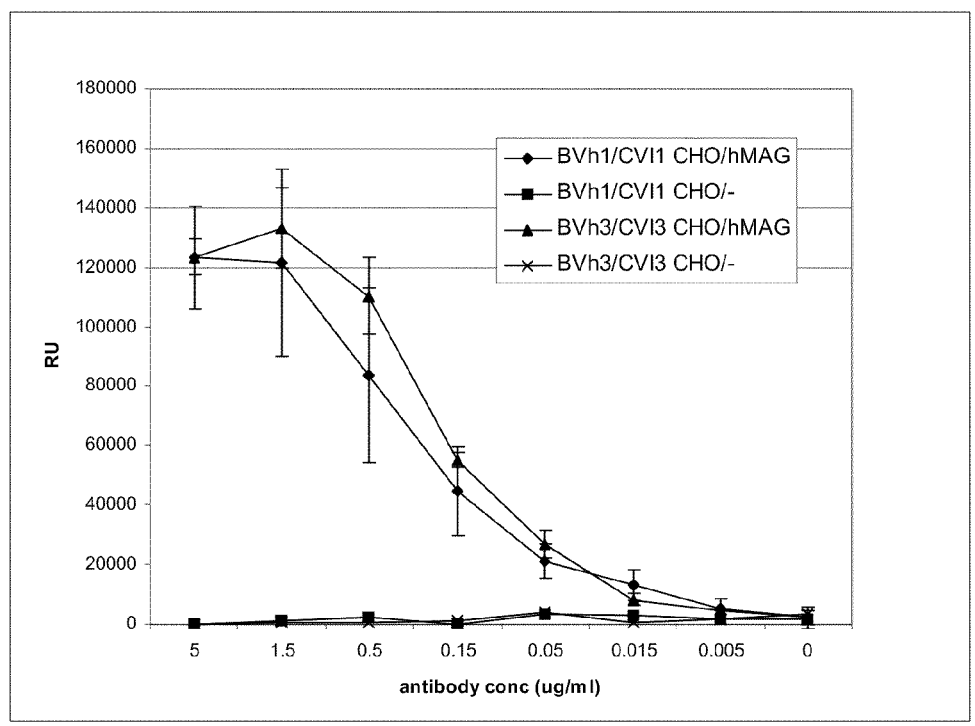
FIG. 8: Humanised anti-MAG antibodies bind to human MAG

FIG. 8 shows that both antibodies tested here are recognising human MAG and are very similar in their binding characteristics. CHO/– are negative controls of CHO cells with no MAG expressed.

Method for Eu Cell-Based ELISA 96-well plates (Costar 3595) were filled with 100 µl cell suspension/well (see table below for recommended cell number for performing assay on days 1, 2, 3 or 4).

| Day | cell number/ml |
| --- | --- |
| 1 | 3 × 105 |
| 2 | 1 × 105 |
| 3 | 5 × 104 |
| 4 | 1 × 104 |

Culture medium was removed and plates blocked with DMEM/F12 (Sigma D6421) containing FCS (10%), BSA (1%), NaN3 (1%; blocking buffer) for 1 hour at RT. Blocking solution was then removed and sample added (in blocking buffer 50 µl/well). Incubated samples at 4° C. for 1 h. Plates were then washed 3× with PBS using a Skatron plate washer. After wash, cells were fixed with 0.5% paraformaldehyde (diluted in PBS) for 20 minutes at 4° C. and again washed as above. 50 µl/well Europium-conjugated secondary antibody diluted in Europium buffer (50 mM Tris base, 150 mM NaCl, 0.5% BSA, 0.1 g/l, Tween 20, 7.86 mg/l DTPA at pH 7.3) was added and incubated for 1 h at 4° C.

Washed plates as above and added 200 µl Delphia enhancement solution/well. Incubated solution at RT for 5-10 minutes. Wells were read within 24 hours on a Victor.

4) Competition ELISA for Binding to Rat MAG-Fc Fusion Protein of Two Purified Humanised Antibodies and the Non-Humanised Mouse Monoclonal Antibody Method 96-well Nunc Maxisorp plates were coated overnight at 4° C. with rat MAG-Fc fusion protein (2.5 µg/ml; R&D Systems; Cat.No. 538-MG) in PBS. Plates were washed twice with PBS containing Tween20 (0.1% v/v; PBST) and blocked with PBS containing BSA (1% w/v) for 1 h at room temperature (RT). Purified humanised antibody was adjusted to a concentration of 200 ng/ml and mixed at equal volume with competitor molecules made up in blocking buffer ranging from 6000 to 0 ng/ml. Competitors were either parental mouse monoclonal antibody (anti-MAG) or an unrelated mouse monoclonal antibody (INN1) at the same concentrations (BVh1/CVl1 only). Antibody/competitor solutions were incubated 1 h at RT and plates then washed 3× with PBST. Secondary antibody (Goat anti-human light chain specific-peroxidase conjugate; Sigma A-7164) was added diluted 1/5000 in blocking buffer and incubated for 1 h at RT. Wells were washed three times as above and binding detected by adding substrate (OPD tablets dissolved according to instructions; Sigma P-9187). Colour development was measured at 490 nm.

Figure 9:
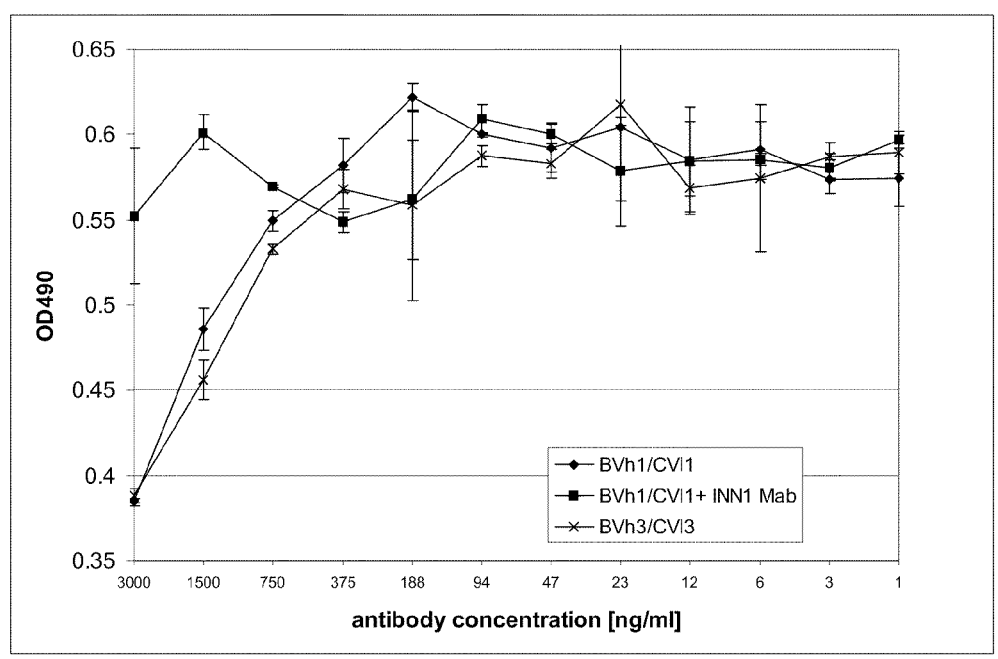
FIG. 9: Competition ELISA with mouse and humanised anti-MAG antibodies MAG

Results:

Both purified antibody preparations are equally competed by the original mouse monoclonal antibody but not by a mouse monoclonal antibody that has an unrelated specificity—see FIG. 9. This shows that the original mouse monoclonal antibody and the humanised antibodies tested here are probably recognising the same epitope and possibly have very similar affinities to rat MAG.

What we claim is:

1. A humanised anti-MAG antibody or functional fragment thereof which binds to and neutralizes MAG and which comprises:
   a heavy chain variable domain comprising:
   hypervariable regions CDRH1 (SEQ ID NO. 4), CDRH2 (SEQ ID NO. 5) and CDRH3 (SEQ ID NO. 6) and
   a light chain variable domain comprising hypervariable regions CDRL1 (SEQ ID NO. 1), CDRL2 (SEQ ID NO. 2) and CDRL3 (SEQ ID NO. 3).

2. The humanised anti-MAG antibody or functional fragment thereof which binds to and neutralizes MAG according to claim 1, wherein the humanised anti-MAG antibody is monoclonal.

3. A humanised anti-MAG antibody or functional fragment thereof which binds to and neutralizes MAG according to claim 1, wherein the heavy chain variable domain comprises one of the following amino acid sequences selected from the group consisting of: SEQ ID No. 13, SEQ ID No. 14, and SEQ ID No. 15.

4. A humanised anti-MAG antibody or functional fragment thereof which binds to and neutralizes MAG according to claim 1, wherein the light chain variable domain comprises one of the following amino acid sequences selected from the group consisting of: SEQ ID No. 16, SEQ ID No. 17, SEQ ID No. 18, and SEQ ID No. 19.

5. A pharmaceutical composition comprising a humanised anti-MAG antibody or functional fragment thereof which binds to and neutralizes MAG according to claim 1, 2, 3, or 4, further comprising a pharmaceutically acceptable diluent or carrier.

6. The humanised anti-MAG antibody or functional fragment thereof which binds to and neutralizes MAG according to claim 1, 2, 3, or 4, further comprising a constant part or fragment thereof of a human light chain and a constant part or fragment thereof of a human heavy chain.

* * * * *

```
                              SEQUENCE LISTING

<160> NUMBER OF SEQ ID NOS: 32

<210> SEQ ID NO 1
<211> LENGTH: 17
<212> TYPE: PRT
<213> ORGANISM: Artificial sequence
<220> FEATURE:
<223> OTHER INFORMATION: Light chain CDR

<400> SEQUENCE: 1

Lys Ser Ser His Ser Val Leu Tyr Ser Ser Asn Gln Lys Asn Tyr Leu
1               5                   10                  15

Ala

<210> SEQ ID NO 2
<211> LENGTH: 7
<212> TYPE: PRT
<213> ORGANISM: Artificial sequence
<220> FEATURE:
<223> OTHER INFORMATION: Light chain CDR

<400> SEQUENCE: 2

Trp Ala Ser Thr Arg Glu Ser
1               5

<210> SEQ ID NO 3
<211> LENGTH: 8
<212> TYPE: PRT
<213> ORGANISM: Artificial sequence
<220> FEATURE:
<223> OTHER INFORMATION: Light chain CDR

<400> SEQUENCE: 3

His Gln Tyr Leu Ser Ser Leu Thr
1               5

<210> SEQ ID NO 4
<211> LENGTH: 5
<212> TYPE: PRT
<213> ORGANISM: Artificial sequence
<220> FEATURE:
<223> OTHER INFORMATION: Heavy chain CDR

<400> SEQUENCE: 4

Asn Tyr Gly Met Asn
1               5

<210> SEQ ID NO 5
<211> LENGTH: 17
<212> TYPE: PRT
<213> ORGANISM: Artificial sequence
<220> FEATURE:
<223> OTHER INFORMATION: Heavy chain CDR

<400> SEQUENCE: 5

Trp Ile Asn Thr Tyr Thr Gly Glu Pro Thr Tyr Ala Asp Asp Phe Thr
1               5                   10                  15

Gly

<210> SEQ ID NO 6
<211> LENGTH: 17
<212> TYPE: PRT
```

<213> ORGANISM: Artificial sequence
<220> FEATURE:
<223> OTHER INFORMATION: Heavy chain CDR

<400> SEQUENCE: 6

Asn Pro Ile Asn Tyr Tyr Gly Ile Asn Tyr Glu Gly Tyr Val Met Asp
1               5                   10                  15

Tyr

<210> SEQ ID NO 7
<211> LENGTH: 51
<212> TYPE: DNA
<213> ORGANISM: Artificial sequence
<220> FEATURE:
<223> OTHER INFORMATION: Polynucleotide encoding CDRL1

<400> SEQUENCE: 7
aagagcagcc acagcgtgct gtacagcagc aaccagaaga actacctggc c          51

<210> SEQ ID NO 8
<211> LENGTH: 21
<212> TYPE: DNA
<213> ORGANISM: Artificial sequence
<220> FEATURE:
<223> OTHER INFORMATION: Polynucleotide encoding CDRL2

<400> SEQUENCE: 8
tgggccagca cccgcgagag c                                           21

<210> SEQ ID NO 9
<211> LENGTH: 24
<212> TYPE: DNA
<213> ORGANISM: Artificial sequence
<220> FEATURE:
<223> OTHER INFORMATION: Polynucleotide encoding CDRL3

<400> SEQUENCE: 9
caccagtacc tgagcagcct gacc                                        24

<210> SEQ ID NO 10
<211> LENGTH: 15
<212> TYPE: DNA
<213> ORGANISM: Artificial sequence
<220> FEATURE:
<223> OTHER INFORMATION: Polynucleotide encoding CDRH1

<400> SEQUENCE: 10
aactacggca tgaac                                                  15

<210> SEQ ID NO 11
<211> LENGTH: 51
<212> TYPE: DNA
<213> ORGANISM: Artificial sequence
<220> FEATURE:
<223> OTHER INFORMATION: Polynucleotide encoding CDRH2

<400> SEQUENCE: 11
tggatcaaca cctacaccgg cgagcccacc tacgccgacg acttcaccgg c          51

<210> SEQ ID NO 12
<211> LENGTH: 51
<212> TYPE: DNA
<213> ORGANISM: Artificial sequence
<220> FEATURE:
<223> OTHER INFORMATION: Polynucleotide encoding CDRH3

<400> SEQUENCE: 12

```
aacccatca actactacgg catcaactac gagggctacg tgatggacta c        51
```

<210> SEQ ID NO 13
<211> LENGTH: 126
<212> TYPE: PRT
<213> ORGANISM: Artificial sequence
<220> FEATURE:
<223> OTHER INFORMATION: Humanised antibody heavy chain variable region

<400> SEQUENCE: 13

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asn Pro Ile Asn Tyr Tyr Gly Ile Asn Tyr Glu Gly Tyr Val
            100                 105                 110

Met Asp Tyr Trp Gly Gln Gly Thr Leu Val Thr Val Ser Ser
        115                 120                 125
```

<210> SEQ ID NO 14
<211> LENGTH: 126
<212> TYPE: PRT
<213> ORGANISM: Artificial sequence
<220> FEATURE:
<223> OTHER INFORMATION: Humanised antibody heavy chain variable region

<400> SEQUENCE: 14

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asn Pro Ile Asn Tyr Tyr Gly Ile Asn Tyr Glu Gly Tyr Val
            100                 105                 110

Met Asp Tyr Trp Gly Gln Gly Thr Leu Val Thr Val Ser Ser
        115                 120                 125
```

<210> SEQ ID NO 15
<211> LENGTH: 126
<212> TYPE: PRT
<213> ORGANISM: Artificial sequence
<220> FEATURE:
<223> OTHER INFORMATION: Humanised antibody heavy chain variable region

<400> SEQUENCE: 15

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Thr Tyr Phe Cys
            85                  90                  95

Ala Arg Asn Pro Ile Asn Tyr Tyr Gly Ile Asn Tyr Glu Gly Tyr Val
            100                 105                 110

Met Asp Tyr Trp Gly Gln Gly Thr Leu Val Thr Val Ser Ser
        115                 120                 125

<210> SEQ ID NO 16
<211> LENGTH: 115
<212> TYPE: PRT
<213> ORGANISM: Artificial sequence
<220> FEATURE:
<223> OTHER INFORMATION: Humanised antibody light chain variable region

<400> SEQUENCE: 16

Asp Ile Val Met Thr Gln Ser Pro Asp Ser Leu Ala Val Ser Leu Gly
1               5                   10                  15

Glu Arg Ala Thr Ile Asn Cys Lys Ser Ser His Ser Val Leu Tyr Ser
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
            85                  90                  95

Tyr Leu Ser Ser Leu Thr Phe Gly Gln Gly Thr Lys Leu Glu Ile Lys
            100                 105                 110

Arg Thr Val
        115

<210> SEQ ID NO 17
<211> LENGTH: 115
<212> TYPE: PRT
<213> ORGANISM: Artificial sequence
<220> FEATURE:
<223> OTHER INFORMATION: Humanised antibody light chain variable region

<400> SEQUENCE: 17

Asp Ile Val Met Thr Gln Ser Pro Asp Ser Leu Ala Val Ser Leu Gly
1               5                   10                  15

Glu Arg Ala Thr Ile Asn Cys Lys Ser Ser His Ser Val Leu Tyr Ser
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60
```

Pro Asp Arg Phe Ser Gly Ser Gly Ser Gly Thr Asp Phe Thr Leu Thr
65                  70                  75                  80

Ile Ile Asn Leu Gln Ala Glu Asp Val Ala Val Tyr Tyr Cys His Gln
                85                  90                  95

Tyr Leu Ser Ser Leu Thr Phe Gly Gln Gly Thr Lys Leu Glu Ile Lys
            100                 105                 110

Arg Thr Val
        115

<210> SEQ ID NO 18
<211> LENGTH: 115
<212> TYPE: PRT
<213> ORGANISM: Artificial sequence
<220> FEATURE:
<223> OTHER INFORMATION: Humanised antibody light chain variable region

<400> SEQUENCE: 18

Asp Ile Val Met Thr Gln Ser Pro Asp Ser Leu Ala Val Ser Leu Gly
1               5                   10                  15

Glu Arg Ala Thr Ile Asn Cys Lys Ser Ser His Ser Val Leu Tyr Ser
                20                  25                  30

Ser Asn Gln Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu His Thr Glu Asp Val Ala Val Tyr Tyr Cys His Gln
                85                  90                  95

Tyr Leu Ser Ser Leu Thr Phe Gly Gln Gly Thr Lys Leu Glu Ile Lys
            100                 105                 110

Arg Thr Val
        115

<210> SEQ ID NO 19
<211> LENGTH: 115
<212> TYPE: PRT
<213> ORGANISM: Artificial sequence
<220> FEATURE:
<223> OTHER INFORMATION: Humanised antibody light chain variable region

<400> SEQUENCE: 19

Asp Ile Val Met Thr Gln Ser Pro Asp Ser Leu Ala Val Ser Leu Gly
1               5                   10                  15

Glu Arg Ala Thr Ile Asn Cys Lys Ser Ser His Ser Val Leu Tyr Ser
                20                  25                  30

Ser Asn Gln Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ile Asn Leu His Thr Glu Asp Val Ala Val Tyr Tyr Cys His Gln
                85                  90                  95

Tyr Leu Ser Ser Leu Thr Phe Gly Gln Gly Thr Lys Leu Glu Ile Lys
            100                 105                 110

Arg Thr Val
        115

<210> SEQ ID NO 20
<211> LENGTH: 378
<212> TYPE: DNA
<213> ORGANISM: Artificial sequence
<220> FEATURE:
<223> OTHER INFORMATION: Polynucleotide sequence encoding the amino acid
      sequence SEQ ID NO: 13

<400> SEQUENCE: 20
caggtgcagc tggtgcaatc tgggtctgag ttgaagaagc ctggggcctc agtgaaggtt     60
tcctgcaagg cttctggata caccttcact aactacggca tgaactgggt gcgacaggcc    120
cctggacaag ggcttgagtg gatgggatgg atcaacacct acaccggcga gcccacctac    180
gccgacgact tcaccggccg gtttgtcttc ccttggaca cctctgtcag cacggcatat    240
ctgcagatca gcagcctaaa ggctgaggac actgccgtgt attactgtgc gagaaacccc    300
atcaactact acggcatcaa ctacgagggc tacgtgatgg actactgggg ccagggcaca    360
ctagtcacag tctcctca                                                 378

<210> SEQ ID NO 21
<211> LENGTH: 378
<212> TYPE: DNA
<213> ORGANISM: Artificial sequence
<220> FEATURE:
<223> OTHER INFORMATION: Polynucleotide sequence encoding the amino acid
      sequence SEQ ID NO: 14

<400> SEQUENCE: 21
caggtgcagc tggtgcaatc tgggtctgag ttgaagaagc ctggggcctc agtgaaggtt     60
tcctgcaagg cttctggata caccttcact aactacggca tgaactgggt gcgacaggcc    120
cctggacaag ggcttgagtg gatgggatgg atcaacacct acaccggcga gcccacctac    180
gccgacgact tcaccggccg gtttgtcttc ccttggaca cctctgtcag cacggcatat    240
ctgcagatca gcagcctaaa ggctgaggac actgccgtgt atttctgtgc gagaaacccc    300
atcaactact acggcatcaa ctacgagggc tacgtgatgg actactgggg ccagggcaca    360
ctagtcacag tctcctca                                                 378

<210> SEQ ID NO 22
<211> LENGTH: 378
<212> TYPE: DNA
<213> ORGANISM: Artificial sequence
<220> FEATURE:
<223> OTHER INFORMATION: Polynucleotide sequence encoding the amino acid
      sequence SEQ ID NO: 15

<400> SEQUENCE: 22
caggtgcagc tggtgcaatc tgggtctgag ttgaagaagc ctggggcctc agtgaaggtt     60
tcctgcaagg cttctggata caccttcact aactacggca tgaactgggt gcgacaggcc    120
cctggacaag ggcttgagtg gatgggatgg atcaacacct acaccggcga gcccacctac    180
gccgacgact tcaccggccg gtttgtcttc ccttggaca cctctgtcag cacggcatat    240
ctgcagatca gcagcctaaa ggctgaggac actgccacct atttctgtgc gagaaacccc    300
atcaactact acggcatcaa ctacgagggc tacgtgatgg actactgggg ccagggcaca    360
ctagtcacag tctcctca                                                 378

<210> SEQ ID NO 23
<211> LENGTH: 345
<212> TYPE: DNA

<213> ORGANISM: Artificial sequence
<220> FEATURE:
<223> OTHER INFORMATION: Polynucleotide sequence encoding the amino acid
      sequence SEQ ID NO: 16

<400> SEQUENCE: 23

| gacatcgtga tgacccagtc tccagactcc ctggctgtgt ctctgggcga gagggccacc | 60 |
| atcaactgca agagcagcca gcgtgctg tacagcagca accagaagaa ctacctggcc | 120 |
| tggtaccagc agaaaccagg acagcctcct aagctgctca tttactgggc atctacccgg | 180 |
| gaatccgggg tccctgaccg attcagtggc agcgggtctg ggacagattt cactctcacc | 240 |
| atcagcagcc tgcaggctga agatgtggca gtttattact gtcaccagta cctgagcagc | 300 |
| ctgacctttg gccaggggac caagctggag atcaaacgta cggtg | 345 |

<210> SEQ ID NO 24
<211> LENGTH: 345
<212> TYPE: DNA
<213> ORGANISM: Artificial sequence
<220> FEATURE:
<223> OTHER INFORMATION: Polynucleotide sequence encoding the amino acid
      sequence SEQ ID NO: 17

<400> SEQUENCE: 24

| gacatcgtga tgacccagtc tccagactcc ctggctgtgt ctctgggcga gagggccacc | 60 |
| atcaactgca agagcagcca gcgtgctg tacagcagca accagaagaa ctacctggcc | 120 |
| tggtaccagc agaaaccagg acagcctcct aagctgctca tttactgggc atctacccgg | 180 |
| gaatccgggg tccctgaccg attcagtggc agcgggtctg ggacagattt cactctcacc | 240 |
| atcatcaacc tgcaggctga agatgtggca gtttattact gtcaccagta cctgagcagc | 300 |
| ctgacctttg gccaggggac caagctggag atcaaacgta cggtg | 345 |

<210> SEQ ID NO 25
<211> LENGTH: 345
<212> TYPE: DNA
<213> ORGANISM: Artificial sequence
<220> FEATURE:
<223> OTHER INFORMATION: Polynucleotide sequence encoding the amino acid
      sequence SEQ ID NO: 18

<400> SEQUENCE: 25

| gacatcgtga tgacccagtc tccagactcc ctggctgtgt ctctgggcga gagggccacc | 60 |
| atcaactgca agagcagcca gcgtgctg tacagcagca accagaagaa ctacctggcc | 120 |
| tggtaccagc agaaaccagg acagcctcct aagctgctca tttactgggc atctacccgg | 180 |
| gaatccgggg tccctgaccg attcagtggc agcgggtctg ggacagattt cactctcacc | 240 |
| atcagcagcc tgcacaccga agatgtggca gtttattact gtcaccagta cctgagcagc | 300 |
| ctgacctttg gccaggggac caagctggag atcaaacgta cggtg | 345 |

<210> SEQ ID NO 26
<211> LENGTH: 345
<212> TYPE: DNA
<213> ORGANISM: Artificial sequence
<220> FEATURE:
<223> OTHER INFORMATION: Polynucleotide sequence encoding the amino acid
      sequence SEQ ID NO: 19

<400> SEQUENCE: 26

| gacatcgtga tgacccagtc tccagactcc ctggctgtgt ctctgggcga gagggccacc | 60 |
| atcaactgca agagcagcca gcgtgctg tacagcagca accagaagaa ctacctggcc | 120 |

-continued

```
tggtaccagc agaaaccagg acagcctcct aagctgctca tttactgggc atctacccgg    180
gaatccgggg tccctgaccg attcagtggc agcgggtctg ggacagattt cactctcacc    240
atcatcaacc tgcacaccga agatgtggca gtttattact gtcaccagta cctgagcagc    300
ctgacctttg gccaggggac caagctggag atcaaacgta cggtg                   345
```

<210> SEQ ID NO 27
<211> LENGTH: 475
<212> TYPE: PRT
<213> ORGANISM: Artificial sequence
<220> FEATURE:
<223> OTHER INFORMATION: Mouse/human chimeric anti-MAG antibody heavy
      chain

<400> SEQUENCE: 27

```
Met Gly Trp Ser Cys Ile Ile Leu Phe Leu Val Ala Thr Ala Thr Gly
1               5                   10                  15

Val His Ser Glu Ile Gln Leu Val Gln Ser Gly Pro Glu Leu Lys Lys
            20                  25                  30

Pro Gly Glu Thr Asn Lys Ile Ser Cys Lys Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Tyr Thr Gly Glu Pro Thr Tyr Ala
65                  70                  75                  80

Asp Asp Phe Thr Gly Arg Phe Ala Phe Ser Leu Glu Thr Ser Ala Ser
                85                  90                  95

Thr Ala Tyr Leu Gln Ile Ser Asn Leu Lys Asn Glu Asp Thr Ala Thr
            100                 105                 110

Tyr Phe Cys Ala Arg Asn Pro Ile Asn Tyr Tyr Gly Ile Asn Tyr Glu
        115                 120                 125

Gly Tyr Val Met Asp Tyr Trp Gly Gln Gly Thr Leu Val Thr Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr Cys Pro Pro
                245                 250                 255

Cys Pro Ala Pro Glu Leu Ala Gly Ala Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
```

```
                    325                 330                 335
Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
            355                 360                 365

Gly Gln Pro Arg Glu Pro Gln Val Tyr Thr Leu Pro Pro Ser Arg Asp
            370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                    405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
            435                 440                 445

Asn Val Phe Ser Cys Ser Val Met His Glu Ala Leu His Asn His Tyr
            450                 455                 460

Thr Gln Lys Ser Leu Ser Leu Ser Pro Gly Lys
465                 470                 475

<210> SEQ ID NO 28
<211> LENGTH: 238
<212> TYPE: PRT
<213> ORGANISM: Artificial sequence
<220> FEATURE:
<223> OTHER INFORMATION: Mouse/human chimeric anti-MAG antibody light
      chain

<400> SEQUENCE: 28

Met Gly Trp Ser Cys Ile Ile Leu Phe Leu Val Ala Thr Ala Thr Gly
1               5                   10                  15

Val His Ser Asn Ile Met Met Thr Gln Ser Pro Ser Ser Leu Ala Val
            20                  25                  30

Ser Ala Gly Glu Lys Val Thr Met Ser Cys Lys Ser Ser His Ser Val
        35                  40                  45

Leu Tyr Ser Ser Asn Gln Lys Asn Tyr Leu Ala Trp Tyr Gln Gln Lys
    50                  55                  60

Pro Gly Gln Ser Pro Lys Leu Leu Ile Tyr Trp Ala Ser Thr Arg Glu
65                  70                  75                  80

Ser Gly Val Pro Asp Arg Phe Thr Gly Ser Gly Ser Gly Thr Asp Phe
                85                  90                  95

Thr Leu Thr Ile Ile Asn Val His Thr Glu Asp Leu Ala Val Tyr Tyr
            100                 105                 110

Cys His Gln Tyr Leu Ser Ser Leu Thr Phe Gly Thr Gly Thr Lys Leu
            115                 120                 125

Glu Ile Lys Arg Thr Val Ala Ala Pro Ser Val Phe Ile Phe Pro Pro
        130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
```

Leu Ser Ser Pro Val Thr Lys Ser Phe Asn Arg Gly Glu Cys
225                 230                 235

<210> SEQ ID NO 29
<211> LENGTH: 475
<212> TYPE: PRT
<213> ORGANISM: Artificial sequence
<220> FEATURE:
<223> OTHER INFORMATION: Mouse/human chimeric anti-MAG antibody heavy
      chain

<400> SEQUENCE: 29

Met Gly Trp Ser Cys Ile Ile Leu Phe Leu Val Ala Thr Ala Thr Gly
1               5                   10                  15

Val His Ser Glu Ile Gln Leu Val Gln Ser Gly Pro Glu Leu Lys Lys
            20                  25                  30

Pro Gly Glu Thr Asn Lys Ile Ser Cys Lys Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Tyr Thr Gly Glu Pro Thr Tyr Ala
65                  70                  75                  80

Asp Asp Phe Thr Gly Arg Phe Ala Phe Ser Leu Glu Thr Ser Ala Ser
                85                  90                  95

Thr Ala Tyr Leu Gln Ile Ser Asn Leu Lys Asn Glu Asp Thr Ala Thr
            100                 105                 110

Tyr Phe Cys Ala Arg Asn Pro Ile Asn Tyr Tyr Gly Ile Asn Tyr Glu
        115                 120                 125

Gly Tyr Val Met Asp Tyr Trp Gly Gln Gly Thr Leu Val Thr Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser

```
                    340                 345                 350
Asn Lys Ala Leu Pro Ala Pro Ile Glu Lys Thr Ile Ser Lys Ala Lys
                355                 360                 365
Gly Gln Pro Arg Glu Pro Gln Val Tyr Thr Leu Pro Pro Ser Arg Asp
            370                 375                 380
Glu Leu Thr Lys Asn Gln Val Ser Leu Thr Cys Leu Val Lys Gly Phe
385                 390                 395                 400
Tyr Pro Ser Asp Ile Ala Val Glu Trp Glu Ser Asn Gly Gln Pro Glu
                405                 410                 415
Asn Asn Tyr Lys Thr Thr Pro Pro Val Leu Asp Ser Asp Gly Ser Phe
            420                 425                 430
Phe Leu Tyr Ser Lys Leu Thr Val Asp Lys Ser Arg Trp Gln Gln Gly
            435                 440                 445
Asn Val Phe Ser Cys Ser Val Met His Glu Ala Leu His Asn His Tyr
            450                 455                 460
Thr Gln Lys Ser Leu Ser Leu Ser Pro Gly Lys
465                 470                 475

<210> SEQ ID NO 30
<211> LENGTH: 475
<212> TYPE: PRT
<213> ORGANISM: Artificial sequence
<220> FEATURE:
<223> OTHER INFORMATION: Humanised anti-MAG antibody

<400> SEQUENCE: 30

Met Gly Trp Ser Cys Ile Ile Leu Phe Leu Val Ala Thr Ala Thr Gly
1               5                   10                  15
Val His Ser Gln Val Gln Leu Val Gln Ser Gly Ser Glu Leu Lys Lys
            20                  25                  30
Pro Gly Ala Ser Val Lys Val Ser Cys Lys Ala Ser Gly Tyr Thr Phe
        35                  40                  45
Thr Asn Tyr Gly Met Asn Trp Val Arg Gln Ala Pro Gly Gln Gly Leu
    50                  55                  60
Glu Trp Met Gly Trp Ile Asn Thr Tyr Thr Gly Glu Pro Thr Tyr Ala
65                  70                  75                  80
Asp Asp Phe Thr Gly Arg Phe Val Phe Ser Leu Asp Thr Ser Val Ser
                85                  90                  95
Thr Ala Tyr Leu Gln Ile Ser Ser Leu Lys Ala Glu Asp Thr Ala Val
            100                 105                 110
Tyr Tyr Cys Ala Arg Asn Pro Ile Asn Tyr Tyr Gly Ile Asn Tyr Glu
            115                 120                 125
Gly Tyr Val Met Asp Tyr Trp Gly Gln Gly Thr Leu Val Thr Val Ser
        130                 135                 140
Ser Ala Ser Thr Lys Gly Pro Ser Val Phe Pro Leu Ala Pro Ser Ser
145                 150                 155                 160
Lys Ser Thr Ser Gly Gly Thr Ala Ala Leu Gly Cys Leu Val Lys Asp
                165                 170                 175
Tyr Phe Pro Glu Pro Val Thr Val Ser Trp Asn Ser Gly Ala Leu Thr
            180                 185                 190
Ser Gly Val His Thr Phe Pro Ala Val Leu Gln Ser Ser Gly Leu Tyr
        195                 200                 205
Ser Leu Ser Ser Val Val Thr Val Pro Ser Ser Ser Leu Gly Thr Gln
    210                 215                 220
Thr Tyr Ile Cys Asn Val Asn His Lys Pro Ser Asn Thr Lys Val Asp
225                 230                 235                 240
```

Lys Lys Val Glu Pro Lys Ser Cys Asp Lys Thr His Thr Cys Pro Pro
            245                 250                 255

Cys Pro Ala Pro Glu Leu Ala Gly Ala Pro Ser Val Phe Leu Phe Pro
            260                 265                 270

Pro Lys Pro Lys Asp Thr Leu Met Ile Ser Arg Thr Pro Glu Val Thr
            275                 280                 285

Cys Val Val Val Asp Val Ser His Glu Asp Pro Glu Val Lys Phe Asn
            290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
            355                 360                 365

Gly Gln Pro Arg Glu Pro Gln Val Tyr Thr Leu Pro Pro Ser Arg Asp
            370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
            435                 440                 445

Asn Val Phe Ser Cys Ser Val Met His Glu Ala Leu His Asn His Tyr
            450                 455                 460

Thr Gln Lys Ser Leu Ser Leu Ser Pro Gly Lys
465                 470                 475

<210> SEQ ID NO 31
<211> LENGTH: 238
<212> TYPE: PRT
<213> ORGANISM: Artificial sequence
<220> FEATURE:
<223> OTHER INFORMATION: Humanised anti-MAG antibody

<400> SEQUENCE: 31

Met Gly Trp Ser Cys Ile Ile Leu Phe Leu Val Ala Thr Ala Thr Gly
1               5                   10                  15

Val His Ser Asp Ile Val Met Thr Gln Ser Pro Asp Ser Leu Ala Val
            20                  25                  30

Ser Leu Gly Glu Arg Ala Thr Ile Asn Cys Lys Ser Ser His Ser Val
            35                  40                  45

Leu Tyr Ser Ser Asn Gln Lys Asn Tyr Leu Ala Trp Tyr Gln Gln Lys
            50                  55                  60

Pro Gly Gln Pro Pro Lys Leu Leu Ile Tyr Trp Ala Ser Thr Arg Glu
65                  70                  75                  80

Ser Gly Val Pro Asp Arg Phe Ser Gly Ser Gly Ser Gly Thr Asp Phe
                85                  90                  95

Thr Leu Thr Ile Ser Ser Leu Gln Ala Glu Asp Val Ala Val Tyr Tyr
            100                 105                 110

Cys His Gln Tyr Leu Ser Ser Leu Thr Phe Gly Gln Gly Thr Lys Leu
            115                 120                 125

```
Glu Ile Lys Arg Thr Val Ala Ala Pro Ser Val Phe Ile Phe Pro Pro
            130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
                195                 200                 205

Asp Tyr Glu Lys His Lys Val Tyr Ala Cys Glu Val Thr His Gln Gly
            210                 215                 220

Leu Ser Ser Pro Val Thr Lys Ser Phe Asn Arg Gly Glu Cys
225                 230                 235

<210> SEQ ID NO 32
<211> LENGTH: 475
<212> TYPE: PRT
<213> ORGANISM: Artificial sequence
<220> FEATURE:
<223> OTHER INFORMATION: Humanised anti-MAG antibody

<400> SEQUENCE: 32

Met Gly Trp Ser Cys Ile Ile Leu Phe Leu Val Ala Thr Ala Thr Gly
1               5                   10                  15

Val His Ser Gln Val Gln Leu Val Gln Ser Gly Ser Glu Leu Lys Lys
            20                  25                  30

Pro Gly Ala Ser Val Lys Val Ser Cys Lys Ala Ser Gly Tyr Thr Phe
        35                  40                  45

Thr Asn Tyr Gly Met Asn Trp Val Arg Gln Ala Pro Gly Gln Gly Leu
    50                  55                  60

Glu Trp Met Gly Trp Ile Asn Thr Tyr Thr Gly Glu Pro Thr Tyr Ala
65                  70                  75                  80

Asp Asp Phe Thr Gly Arg Phe Val Phe Ser Leu Asp Thr Ser Val Ser
                85                  90                  95

Thr Ala Tyr Leu Gln Ile Ser Ser Leu Lys Ala Glu Asp Thr Ala Val
            100                 105                 110

Tyr Tyr Cys Ala Arg Asn Pro Ile Asn Tyr Tyr Gly Ile Asn Tyr Glu
        115                 120                 125

Gly Tyr Val Met Asp Tyr Trp Gly Gln Gly Thr Leu Val Thr Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr Cys Pro Pro
                245                 250                 255

Cys Pro Ala Pro Glu Leu Leu Gly Gly Pro Ser Val Phe Leu Phe Pro
```

-continued

```
             260                 265                 270
Pro Lys Pro Lys Asp Thr Leu Met Ile Ser Arg Thr Pro Glu Val Thr
        275                 280                 285

Cys Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
            325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Asp
    370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
            405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475
```